(12) United States Patent
Clausen et al.

(10) Patent No.: US 7,531,006 B2
(45) Date of Patent: May 12, 2009

(54) SENSING SYSTEM AND METHOD FOR MOTION-CONTROLLED FOOT UNIT

(75) Inventors: Arinbjörn Viggo Clausen, Reykjavik (IS); Christophe Guy Lecomte, Reykjavik (IS); Larus Sigfusson, Reykjavik (IS)

(73) Assignee: Össur hf, Reykjavik (IS)

( * ) Notice: Subject to any disclaimer, the term of this patent is extended or adjusted under 35 U.S.C. 154(b) by 212 days.

(21) Appl. No.: 11/218,923

(22) Filed: Sep. 1, 2005

(65) Prior Publication Data

US 2007/0050045 A1    Mar. 1, 2007

(51) Int. Cl.
*A61F 2/68* (2006.01)
*A61F 2/66* (2006.01)
*A61F 2/48* (2006.01)

(52) U.S. Cl. .............................. 623/53; 623/24; 623/48
(58) Field of Classification Search ............. 623/47–56; 602/27; 901/2, 46
See application file for complete search history.

(56) References Cited

U.S. PATENT DOCUMENTS

| | | | |
|---|---|---|---|
| 2,568,051 | A | 9/1951 | Catranis |
| 3,820,168 | A | 6/1974 | Horvath |
| 3,995,324 | A | 12/1976 | Burch |
| 4,030,141 | A | 6/1977 | Graupe |
| 4,065,815 | A | 1/1978 | Sen-Jung |
| 4,179,759 | A | 12/1979 | Smith |
| 4,209,860 | A | 7/1980 | Graupe |
| 4,212,087 | A | 7/1980 | Mortensen |
| 4,387,472 | A | 6/1983 | Wilson |
| 4,521,924 | A | 6/1985 | Jacobsen et al. |
| 4,558,704 | A | 12/1985 | Petrofsky |
| 4,569,352 | A | 2/1986 | Petrofsky et al. |
| 4,711,242 | A | 12/1987 | Petrofsky |
| 4,776,852 | A | 10/1988 | Bubic |

(Continued)

FOREIGN PATENT DOCUMENTS

DE    4229330 A1    3/1994

(Continued)

OTHER PUBLICATIONS

Partial International Search, PCT Application No. US2006/033658, mailed Jan. 15, 2007, 2 pages.

(Continued)

*Primary Examiner*—Bruce E Snow
(74) *Attorney, Agent, or Firm*—Knobbe, Martens, Olson & Bear, LLP

(57) ABSTRACT

A system and method for sensing movement of a device associated with a limb. In one example, a prosthetic or orthotic system includes a sensor assembly configured to measure movement of a component of the system in a single direction while substantially isolating negative effects of forces and/or loads in other directions. For instance, the sensor assembly may be advantageously coupled to a pivot assembly configured to substantially mimic a natural ankle joint. The sensor assembly may monitor rotation of a foot unit about an axis of a pivot pin of the pivot assembly and disregard other movements and/or forces. For example, the sensor assembly may include a potentiometer that detects rotation of an associated elongated bellow portion about the axis, wherein the bellow portion includes a plurality of ridges configured to substantially eliminate effects of radial and/or axial forces.

15 Claims, 20 Drawing Sheets

U.S. PATENT DOCUMENTS

| | | |
|---|---|---|
| 4,876,944 A | 10/1989 | Wilson et al. |
| 4,892,554 A | 1/1990 | Robinson |
| 4,944,755 A | 7/1990 | Hennequin et al. |
| 4,994,086 A | 2/1991 | Edwards |
| 5,044,360 A | 9/1991 | Janke |
| 5,062,856 A | 11/1991 | Sawamura et al. |
| 5,062,857 A | 11/1991 | Berringer |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,181,931 A | 1/1993 | Van de Veen |
| 5,201,772 A | 4/1993 | Maxwell |
| 5,217,500 A | 6/1993 | Phillips |
| 5,219,365 A | 6/1993 | Sabolich |
| 5,252,102 A | 10/1993 | Singer et al. |
| 5,336,269 A | 8/1994 | Smits |
| 5,376,133 A | 12/1994 | Gramnäs |
| 5,376,137 A | 12/1994 | Shorter et al. |
| 5,383,939 A | 1/1995 | James |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,443,521 A | 8/1995 | Knoth et al. |
| 5,443,524 A | 8/1995 | Sawamura et al. |
| 5,443,528 A | 8/1995 | Allen |
| 5,472,412 A | 12/1995 | Knoth |
| 5,476,441 A | 12/1995 | Durfee et al. |
| 5,504,415 A | 4/1996 | Podrazhansky et al. |
| 5,545,232 A | 8/1996 | Van de Veen |
| 5,545,233 A | 8/1996 | Fitzlaff |
| 5,571,205 A | 11/1996 | James |
| 5,571,212 A | 11/1996 | Cornelius |
| 5,571,213 A | 11/1996 | Allen |
| 5,586,557 A | 12/1996 | Nelson et al. |
| 5,650,704 A | 7/1997 | Pratt et al. |
| 5,656,915 A | 8/1997 | Eaves |
| 5,662,693 A | 9/1997 | Johnson et al. |
| 5,704,945 A | 1/1998 | Wagner et al. |
| 5,704,946 A | 1/1998 | Greene |
| 5,728,170 A | 3/1998 | Becker et al. |
| 5,746,774 A | 5/1998 | Kramer et al. |
| 5,779,735 A | 7/1998 | Molino |
| 5,800,568 A | 9/1998 | Atkinson et al. |
| 5,888,212 A | 3/1999 | Petrofsky et al. |
| 5,888,213 A | 3/1999 | Sears et al. |
| 5,888,246 A | 3/1999 | Gow |
| 5,893,891 A | 4/1999 | Zahedi |
| 5,895,430 A | 4/1999 | O'Conner |
| 5,919,149 A | 7/1999 | Allum |
| 5,955,667 A | 9/1999 | Fyfe |
| 5,957,981 A | 9/1999 | Gramnäs |
| 5,972,035 A | 10/1999 | Blatchford |
| 5,982,156 A | 11/1999 | Weimer et al. |
| 5,998,930 A | 12/1999 | Upadhyay et al. |
| 6,007,582 A | 12/1999 | May |
| 6,061,577 A | 5/2000 | Andrieu et al. |
| 6,091,977 A | 7/2000 | Tarjan et al. |
| 6,113,642 A | 9/2000 | Petrofsky et al. |
| 6,129,766 A | 10/2000 | Johnson et al. |
| 6,165,226 A | 12/2000 | Wagner |
| 6,183,425 B1 | 2/2001 | Whalen et al. |
| 6,187,051 B1 | 2/2001 | Gerad van de Veen |
| 6,195,921 B1 | 3/2001 | Truong |
| 6,206,932 B1 | 3/2001 | Johnson |
| 6,206,934 B1 | 3/2001 | Phillips |
| 6,241,775 B1 | 6/2001 | Blatchford |
| 6,301,964 B1 | 10/2001 | Fyfe et al. |
| 6,350,286 B1 | 2/2002 | Atkinson et al. |
| 6,361,570 B1 | 3/2002 | Gow |
| 6,373,152 B1 | 4/2002 | Wang et al. |
| 6,409,695 B1 | 6/2002 | Connelly |
| 6,423,098 B1 | 7/2002 | Biedermann |
| 6,425,925 B1 | 7/2002 | Grundel |
| 6,430,843 B1 | 8/2002 | Potter et al. |
| 6,443,993 B1 | 9/2002 | Koniuk |
| 6,443,995 B1 | 9/2002 | Townsend et al. |
| 6,451,481 B1 | 9/2002 | Lee et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,537,322 B1 | 3/2003 | Johnson et al. |
| 6,602,295 B1 | 8/2003 | Doddroe et al. |
| 6,610,101 B2 | 8/2003 | Herr et al. |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,719,806 B1 | 4/2004 | Zahedi et al. |
| 6,740,123 B2 | 5/2004 | Davalli et al. |
| 6,743,260 B2 | 6/2004 | Townsend |
| 6,755,870 B1 | 6/2004 | Biedermann et al. |
| 6,764,520 B2 | 7/2004 | Deffenbaugh et al. |
| 6,770,045 B2 | 8/2004 | Naft et al. |
| 6,876,135 B2 | 4/2005 | Pelrine |
| 7,029,500 B2 | 4/2006 | Martin |
| 7,063,727 B2 | 6/2006 | Phillips et al. |
| 7,131,998 B2 | 11/2006 | Pasolini |
| 7,164,967 B2 | 1/2007 | Etienne-Cummings et al. |
| 7,431,737 B2 | 10/2008 | Ragnarsdottir et al. |
| 2002/0040601 A1 | 4/2002 | Fyfe et al. |
| 2002/0087216 A1 | 7/2002 | Atkinson et al. |
| 2002/0138153 A1 | 9/2002 | Koniuk |
| 2002/0183803 A1 | 12/2002 | Fang et al. |
| 2002/0198604 A1 | 12/2002 | Schulman et al. |
| 2003/0029247 A1 | 2/2003 | Biedermann |
| 2003/0067245 A1 | 4/2003 | Pelrine et al. |
| 2003/0093158 A1 | 5/2003 | Phillips et al. |
| 2003/0120353 A1 | 6/2003 | Christensen |
| 2003/0163206 A1 | 8/2003 | Yasui et al. |
| 2004/0049290 A1 | 3/2004 | Bedard |
| 2004/0054423 A1 | 3/2004 | Martin |
| 2004/0064195 A1 | 4/2004 | Herr |
| 2004/0088057 A1 | 5/2004 | Bedard |
| 2004/0111163 A1 | 6/2004 | Bedard et al. |
| 2004/0181289 A1 | 9/2004 | Bedard |
| 2004/0193286 A1 | 9/2004 | Grundei |
| 2004/0267379 A1 | 12/2004 | Pasolini |
| 2005/0004495 A1 | 1/2005 | Goswami |
| 2005/0010139 A1 | 1/2005 | Aminian et al. |
| 2005/0107889 A1 | 5/2005 | Bedard et al. |
| 2005/0119763 A1 | 6/2005 | Christensen |
| 2005/0143838 A1 | 6/2005 | Collier |
| 2005/0192677 A1 | 9/2005 | Ragnarsdottir et al. |
| 2005/0197717 A1 | 9/2005 | Ragnarsdottir et al. |
| 2005/0283257 A1 | 12/2005 | Bisbee et al. |
| 2006/0041321 A1 | 2/2006 | Christensen |
| 2006/0064195 A1 | 3/2006 | Kern et al. |
| 2006/0122710 A1 | 6/2006 | Bedard |
| 2006/0122711 A1 | 6/2006 | Bedard et al. |
| 2006/0136072 A1 | 6/2006 | Bisbee et al. |
| 2006/0155385 A1 | 7/2006 | Martin |
| 2006/0249315 A1 | 11/2006 | Herr et al. |
| 2007/0016329 A1 | 1/2007 | Herr et al. |
| 2007/0027555 A1 | 2/2007 | Palmer et al. |
| 2007/0043449 A1 | 2/2007 | Herr et al. |
| 2007/0123997 A1 | 5/2007 | Herr et al. |

| | | | |
|---|---|---|---|
| 2007/0162152 A1 | 7/2007 | Herr et al. | |

FOREIGN PATENT DOCUMENTS

| | | |
|---|---|---|
| DE | 19521464 A1 | 6/1995 |
| DE | 19754690 A | 7/1999 |
| EP | 0549855 A2 | 7/1993 |
| EP | 0628296 A2 | 12/1994 |
| EP | 0718951 A | 6/1996 |
| EP | 0902547 A | 3/1999 |
| EP | 1066793 | 1/2001 |
| EP | 1107420 A | 6/2001 |
| EP | 1166726 A1 | 1/2002 |
| EP | 1169982 A1 | 1/2002 |
| EP | 1340478 | 9/2003 |
| FR | 2623086 A1 | 5/1989 |
| GB | 2201260 | 8/1988 |
| GB | 2244006 | 11/1991 |
| GB | 2260495 A | 4/1993 |
| GB | 2301776 | 12/1996 |
| GB | 2302949 A | 2/1997 |
| GB | 2367753 | 8/1998 |
| GB | 2328160 | 2/1999 |
| GB | 2334891 | 9/1999 |
| GB | 2338653 | 12/1999 |
| JP | 11056885 | 3/1999 |
| JP | 11000345 A2 | 6/1999 |
| JP | 2001-1277175 | 10/2001 |
| JP | 2002-191654 A | 7/2002 |
| WO | WO 93/24080 A1 | 12/1993 |
| WO | WO 94/06374 | 3/1994 |
| WO | WO 95-26171 A1 | 10/1995 |
| WO | WO 96/41598 | 12/1996 |
| WO | WO 96/41599 A | 12/1996 |
| WO | WO 97/00661 A1 | 1/1997 |
| WO | WO 98-25552 | 6/1998 |
| WO | WO 98-38951 A1 | 9/1998 |
| WO | WO 99/05991 A2 | 2/1999 |
| WO | WO 99-08621 A2 | 2/1999 |
| WO | WO 99-29272 | 6/1999 |
| WO | WO 00/27318 A | 5/2000 |
| WO | WO 00/30572 A1 | 6/2000 |
| WO | WO 00-38599 | 7/2000 |
| WO | WO 00/71061 | 11/2000 |
| WO | WO 01-17466 A2 | 3/2001 |
| WO | WO 01/50986 A1 | 7/2001 |
| WO | WO 01-72245 | 10/2001 |
| WO | WO 03/003953 | 1/2003 |
| WO | WO 03/086245 A | 10/2003 |
| WO | WO 03-088373 A | 10/2003 |
| WO | WO 2004/017871 | 3/2004 |
| WO | WO 2004/017872 | 3/2004 |
| WO | WO 2004/017873 | 3/2004 |
| WO | WO 2005/041819 A2 | 5/2005 |

OTHER PUBLICATIONS

Townsend M A et al., "Biomechanics and modeling of bipedal climbing and descending." Journal of Biomechanics 1976, vol. 9, No. 4, pp. 227-239, XP00807405.

Au S K et al., "An EMG-Position Controlled System for an Active Ankle-Foot Prosthesis: An Initial Experimental Study" Rehabilitation Robotics, 2005. ICORR 2005., 9th International Conference on Chicago, IL, USA Jun. 28-Jul. 1, 2005, Piscataway, NJ, IEEE, Jun. 28, 2005, pp. 375-379, XP008078417.

International Search Report and Written Opinion, mailed May 11, 2007, International Application No. PCT/2006/0333658, 13 pages.

U.S. Appl. No. 11/367,049, filed Mar. 1, 2006, Clausen et al.

U.S. Appl. No. 11/367,048, filed Mar. 1, 2006, Clausen et al.

U.S. Appl. No. 11/219,317, filed Sep. 1, 2005, Jonsson et al.

Proteor, Assembly and Adjustment Instructions for 1P50-R, Sep. 2004, pp. 1-21, France.

Copes, Bionic Ankle: The Most Significant Development in Ankle Prosthetics in Over a Half Century, 1985, 3 pages, USA.

H. Dietl & H. Bargehr, Der Einsatz von Elektronik bei Prothesen zur Versorgung der unteren Extremitat, Med. Orth. Tech., 1997, pp. 31-35, vol.-issue 117, Gentner Verlag Stuttgart, Austria.

Flowers, et al., Journal of Biomechanical Engineering: Transactions of the ASME; Feb. 1977, pp. 3-8.

Blaya, J. A., et al., "Adaptive Control of a Variable-Impedance Ankle-Foot Orthosis to Assist Drop-Foot Gait" IEEE Transactions on Neural Systems and Rehabilitation Engineering, vol. 12, No. 1, Mar. 2004, pp. 24-31.

Suga, T., et al., "Newly designed computer controlled knee-ankle-foot orthosis (Intelligent Orthosis)", Prosthetics and Orthotics International, 1998, 22, 230-239.

FIG. 10

| Possible Transits: From State to State (402) | Stance | Level Ground Walking | Ascending Stairs | Descending Stairs | Incline (up) | Decline | Sitting Down | Sitting | Standing Up | Adjust Heel Height (404) |
|---|---|---|---|---|---|---|---|---|---|---|
| Stance | N/A | Toe Clearance | -10° | -10° | -2.5°, -5° | +2.5°, +5° | No Action | | | Set Heel Height |
| Level Ground Walking | No Action | N/A | -10° | -10° | -2.5°, -5° | +2.5°, +5° | | | | |
| Ascending Stairs | User Setpoint | Toe Clearance | N/A | N/A | -2.5°, -5° | +2.5°, +5° | | | | |
| Descending Stairs | User Setpoint | Toe Clearance | -10° | | -2.5°, -5° | +2.5°, +5° | | | | |
| Incline (up) | No Action | Toe Clearance | -10° | N/A | N/A | N/A | | | | |
| Decline | No Action | Toe Clearance | | -10° | -2.5°, -5° | | | | | |
| Sitting Down | | | | | | | | Relax Ankle | N/A | |
| Sitting | | | | | | | N/A | | User Setpoint | |
| Standing Up | User Setpoint | Toe Clearance | | | | | | N/A | | Set Heel Height |
| Adjust Heel Height | User Setpoint | | | | | | User Setpoint | User Setpoint | N/A | N/A |

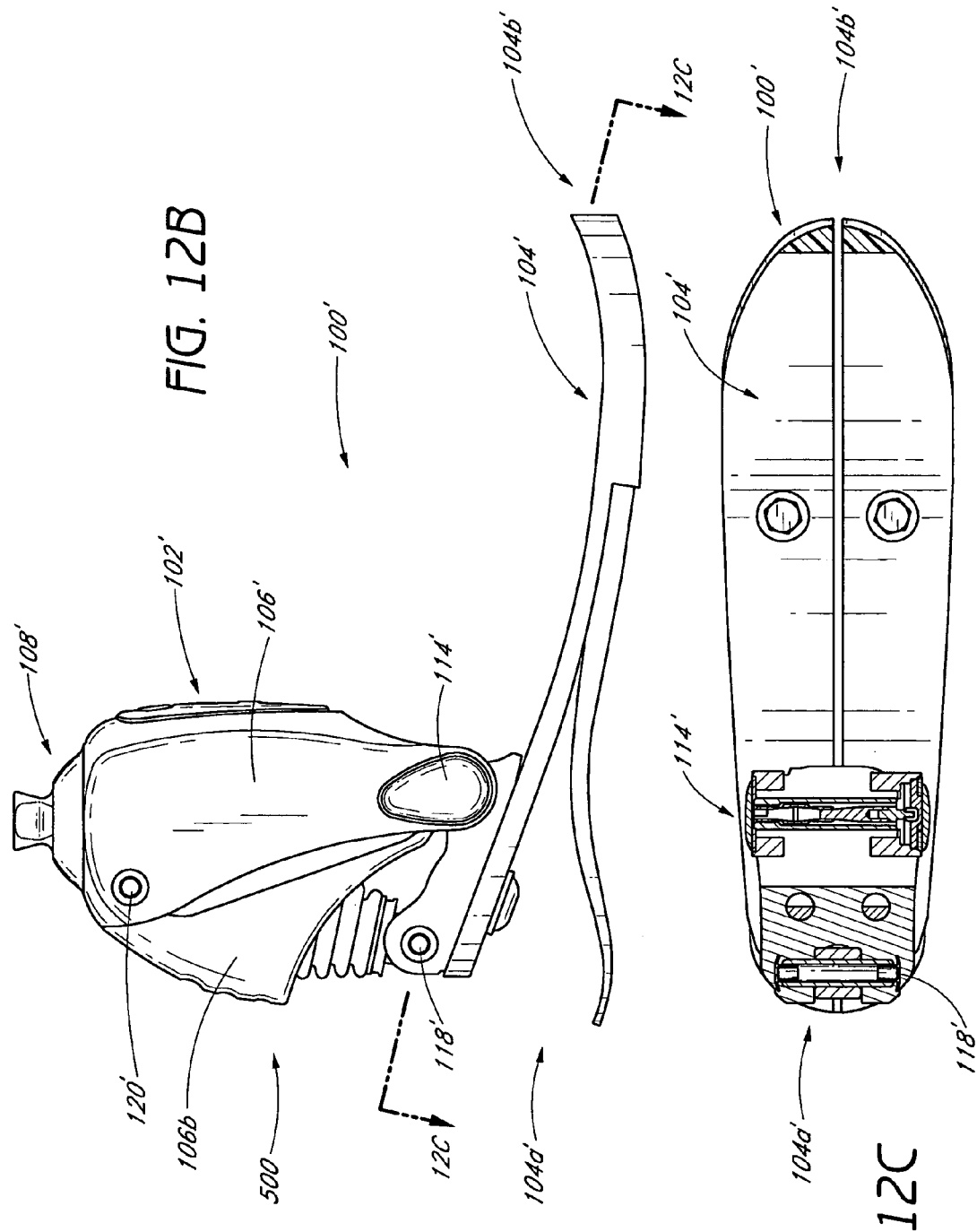

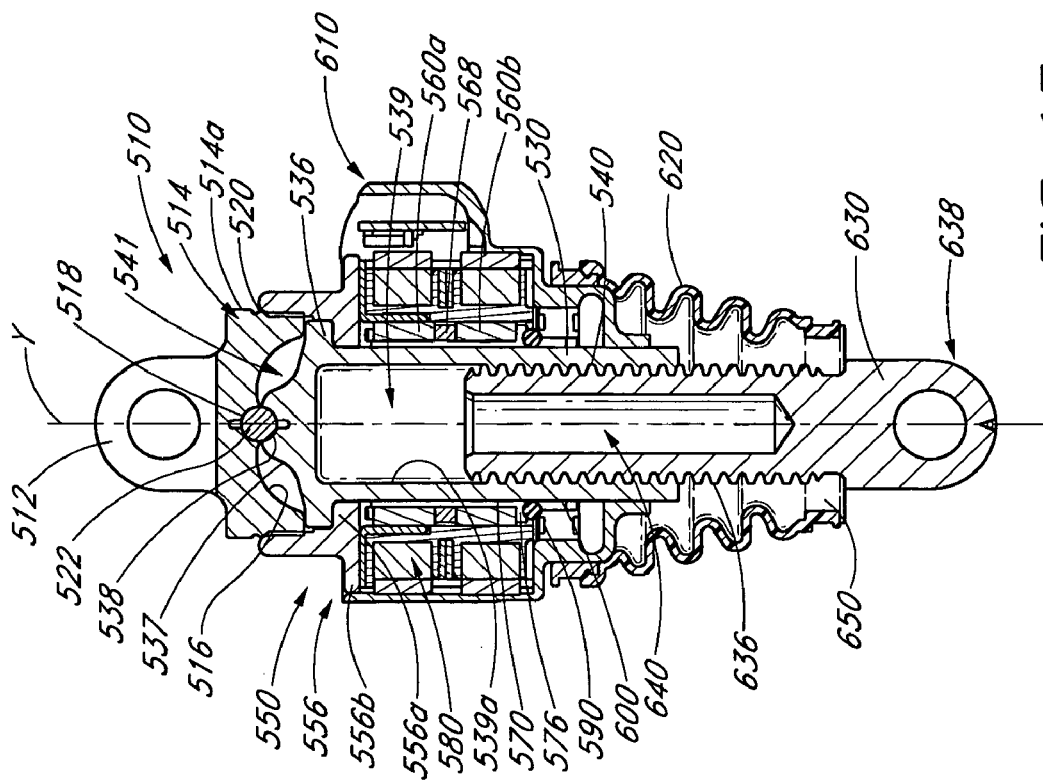
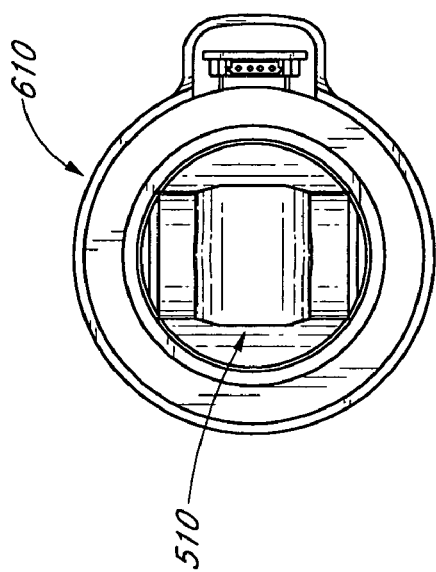
FIG. 17
FIG. 16

SENSING SYSTEM AND METHOD FOR MOTION-CONTROLLED FOOT UNIT

BACKGROUND OF THE INVENTION

1. Field of the Invention

Preferred embodiments of this invention relate to sensing systems and methods for a motion-controlled limb and, in particular, an ankle-motion-controlled foot.

2. Description of the Related Art

Millions of individuals worldwide rely on prosthetic and/or orthotic devices to compensate for disabilities, such as amputation or debilitation, and to assist in the rehabilitation of injured limbs. Orthotic devices include external apparatuses used to support, align, prevent, protect, correct deformities of, or improve the function of movable parts of the body. Prosthetic devices include apparatuses used as artificial substitutes for a missing body part, such as an arm or leg.

The number of disabled persons and amputees is increasing each year as the average age of individuals increases, as does the prevalence of debilitating diseases such as diabetes. As a result, the need for prosthetic and orthotic devices is also increasing. Conventional orthoses are often used to support a joint, such as an ankle or a knee, of an individual, and movement of the orthosis is generally based solely on the energy expenditure of the user. Some conventional prostheses are equipped with basic controllers that artificially mobilize the joints without any interaction from the amputee and are capable of generating only basic motions. Such basic controllers do not take into consideration the dynamic conditions of the working environment. The passive nature of these conventional prosthetic and orthotic devices typically leads to movement instability, high energy expenditure on the part of the disabled person or amputee, gait deviations and other short- and long-term negative effects. This is especially true for leg orthoses and prostheses.

Furthermore, some conventional prosthetic and orthotic devices have at least one sensor associated therewith that is used to monitor movement of the prosthetic/orthotic device or the individual. Such sensors, however, are often subjected to various forces and/or loads that may affect the sensors' readings.

SUMMARY OF THE INVENTION

Accordingly, one embodiment of the invention includes a prosthetic or orthotic system that is self-powered and that mimics the natural movement of a healthy limb, and in particular, the movement of a healthy ankle. Another embodiment of the invention includes a sensor system and a control system that manage the motion of the prosthetic or orthotic system so as to facilitate movement by the disabled person or amputee.

One embodiment of the invention includes a system associated with the movement of a limb. In one embodiment, the system comprises a foot unit; an attachment member having an upper end and a lower end, wherein the lower end is pivotably attached to a first location on the foot unit; and an actuator operatively coupled to the foot unit and to the attachment member, wherein the actuator is configured to actively adjust an angle between the attachment member and the foot unit. For example, the foot unit may be a prosthetic or orthotic device.

Another embodiment of the invention includes a prosthetic system for mimicking the natural movement of an ankle. In one embodiment, the prosthetic system comprises a prosthetic foot; a pivot assembly attached to a first position on the prosthetic foot, wherein the first position is near a natural ankle location of the prosthetic foot; a lower limb member extending in a tibial direction, the lower limb member having an upper end and a lower end, wherein the lower end of the lower limb member is operatively coupled to the pivot assembly; and an actuator operatively coupled to the prosthetic foot and to the lower limb member, wherein the actuator is configured to actively adjust an angle between the lower limb member and the prosthetic foot about the pivot assembly.

One embodiment of the invention includes a method for controlling a device associated with the movement of a limb. In one embodiment, the method comprises monitoring with at least one sensor the movement of an actuatable device associated with a limb; generating data indicative of said movement; processing the data with a processing module to determine a current state of locomotion of the actuatable device; and adjusting the actuatable device based on the determined state of locomotion, wherein said adjusting comprises substantially mimicking the movement of a healthy ankle. For example, the actuatable device may be a prosthesis or an orthosis.

Another embodiment of the invention includes a method for controlling a prosthetic ankle device. In one embodiment, the method comprises monitoring with at least one sensor the movement of an actuatable prosthetic ankle device, wherein the at least one sensor generates data indicative of the movement of the prosthetic ankle device; receiving and processing the data with a control module to determine a current state of locomotion of the actuatable prosthetic ankle device; outputting with the control module at least one control signal based on the determined state of locomotion; and adjusting the actuatable prosthetic ankle device based at least upon the control signal, wherein said adjusting comprises substantially mimicking the movement of a healthy ankle.

In one embodiment, a prosthetic or orthotic system is provided having an ankle-motion-controlled foot. The prosthetic or orthotic system comprises, among other things, a lower limb member, an actuator, and a foot unit. The actuator is configured to mimic the motion of an ankle by adjusting the angle between the lower limb member and the foot unit. The prosthetic or orthotic system also comprises an attachment portion that facilitates coupling of the lower limb member to another prosthetic or orthotic member, to the stump of an amputee, or to another component. The prosthetic or orthotic system may also comprise a rechargeable battery to provide power to the actuator or other components of the system. Embodiments of the invention include systems for both transtibial and transfemoral amputees.

In another embodiment of the invention, the prosthetic or orthotic system comprises a sensor system that is used to capture information regarding the position and movement of the prosthetic or orthotic device. This information may be processed in real-time so as to predict appropriate movements for the prosthetic or orthotic device and to adjust the prosthetic or orthotic device accordingly.

In one embodiment of the invention, a system architecture is provided having a sensor module, a central processing unit, a memory, an external interface, a control drive module, an actuator, and an ankle device. The system architecture may receive instructions and/or data from external sources, such as a user or an electronic device, through the external interface.

In one embodiment, a control system may also be provided that manages the movement of the orthosis or the prosthesis. In one embodiment, the control system manages the movement of an actuator, such as a screw motor. Such motion control provides for movement by the user up inclined surfaces, down declines, or on stairs. In one embodiment, the control system may be configured to monitor through sensors the movements of a healthy limb and use the measurements to control the movement of the prosthesis or orthosis. The control system may also manage the damping of the actuator or other portions of the orthosis or prosthesis.

In one embodiment, a method is provided for controlling actuation of a prosthetic or orthotic device. The method comprises providing one or more sensors on an actuatable prosthetic or orthotic device. Data received from the sensors is processed and is used to determine the current state of locomotion for the prosthetic device. A processing unit, using at least a portion of the data received from the sensors, then predicts movement of the prosthetic or orthotic device. In one embodiment, a prosthetic ankle is provided that mimics the movement of a healthy ankle. The one or more sensors may comprise, for example, gyroscopes and/or accelerometers. In another embodiment of the invention, adjustments are not made to the actuatable prosthetic or orthotic device unless the locomotion type of the user is determined by the processing unit to have a security factor above a predetermined threshold value.

In another embodiment, a method is provided for identifying motion of an orthotic or prosthetic device. The method comprises receiving data from one or more sensors placed on an orthotic or prosthetic device while the device is moving. A waveform is generated from the data received by the sensors. A specific motion for the orthotic or prosthetic device is identified by correlating the waveform with known waveforms for particular types of motion. For example, known waveforms may be inputted by a user or downloaded from an external device or system. The waveforms may also be stored in a memory on the prosthetic or orthotic device.

In another embodiment, a method is provided for actuating an ankle-assisting device. The device is actuated by providing a computer control to provide relative motion between a first and a second portion of the device. In one embodiment, the device is an orthosis. In another embodiment, the device is a prosthesis. In one embodiment, the computer control predicts future motion of the device. In another embodiment, the computer control receives input from at least one sensor module that receives information regarding environmental variables and/or the movement or position of the prosthetic or orthotic device. In another embodiment, the computer control receives input from at least one sensor module that receives information regarding the movement or position of a healthy limb.

One embodiment of the invention includes a device configured to be attached to a limb. The device comprises a first portion and a second portion, the first and second portions being moveable relative to each other to mimic a natural human joint. The device also comprises an actuator coupling the first and second portions together and configured to adjust the angle between the first and second portions. The actuator comprises a rotor operatively coupled to a stator and a motor configured to rotate the rotor, wherein the actuator is selectively locked during a desired phase in a gait cycle.

Another embodiment of the invention includes a device configured to be attached to a limb. The device comprises a first portion and a second portion, the first and second portions being moveable relative to each other to mimic a natural human joint. The device also comprises an actuator coupling the first and second portions together and configured to adjust the angle between the first and second portions. The actuator comprises a rotor operatively coupled to a stator and a motor configured to rotate the rotor. The device also comprises means for minimizing friction against the rotor.

Still another embodiment of the invention includes a device configured to be attached to a limb. The device comprises a first portion and a second portion, the first and second portions being moveable relative to each other to mimic a natural human joint. The device also comprises an actuator coupling the first and second portions together and configured to adjust the angle between the first and second portions. The actuator comprises a rotor operatively coupled to a stator and a motor configured to rotate the rotor, wherein the motor is disposed about the rotor.

Another embodiment of the invention includes a prosthetic device configured to be attached to a limb. The device comprises a prosthetic foot and a pivot assembly attached to the prosthetic foot, the pivot assembly mimicking a natural human ankle joint. The device also comprises a support member having an upper end and a lower end, wherein the lower end of the support member is operatively coupled to the pivot assembly. The prosthetic device also comprises an actuator operatively coupled to the prosthetic foot and the support member, the actuator configured to adjust an angle between the support member and the prosthetic foot about the pivot assembly, wherein the actuator is selectively locked during a desired phase of a gait cycle of the prosthetic foot.

In still another embodiment, an actuator is provided, comprising an elongate member extending about a major axis of the actuator. The actuator also comprises a rotor rotatably coupled to the elongate member and a stator operatively coupled to the rotor. At least one magnet is disposed between the rotor and the stator, the magnet configured to apply a magnetic force between the rotor and the stator. The actuator also comprises a motor configured to rotate the rotor relative to the elongate member, wherein the at least one magnet is configured to minimize friction between the rotor and the stator.

In another embodiment of the invention, an actuator is provided, comprising an elongate member extending about a major axis of the actuator. The actuator also comprises a rotor rotatably coupled to the elongate member and a stator operatively coupled to the rotor. A ball bearing is disposed between the rotor and the stator. The actuator also comprises a motor configured to rotate the rotor relative to the elongate member, wherein the ball bearing is configured to minimize friction between the rotor and the stator.

In yet another embodiment of the invention, an actuator is provided, comprising an elongate member extending about a major axis of the actuator. A rotor is rotatably coupled to the elongate member and a stator operatively coupled to the rotor. The actuator also comprises a motor disposed about the rotor and configured to rotate the rotor relative to the elongate member.

In another embodiment, an actuator is provided, comprising an elongate member extending about a major axis of the actuator. The actuator also comprises a rotor rotatably coupled to the elongate member, a retainer disposed about the rotor, and a stator operatively coupled to the rotor. A motor is configured to rotate the rotor relative to the elongate member, wherein the rotor and the retainer selectively engage to inhibit rotation of the rotor.

In another embodiment, a method of operating a prosthetic device attached to a limb is provided. The method comprises providing a prosthetic device configured to attach to a limb, the device mimicking a natural human joint and having a first portion and a second portion, the portions moveable relative to each other about the joint. The method also comprises providing an actuator coupled to the first portion and the second portion, adjusting an angle between the first portion and the second portion and selectively locking the actuator during a desired phase of a gait cycle.

In still another embodiment, a method of operating a prosthetic device attached to a limb is provided. The method comprises providing a prosthetic device configured to attach to a limb, the device mimicking a natural human joint and having a first portion and a second portion, the portions moveable relative to each other about the joint. The method also comprises providing an actuator coupled to the first portion and the second portion, adjusting an angle between the first portion and the second portion and actively minimizing friction against a rotor of the actuator during a desired phase in a gait cycle.

In another embodiment, a system is disclosed for sensing a rotational movement of a lower-limb prosthetic device. The system includes a prosthetic foot and an attachment member having an upper end and a lower end. The system also includes a pivot assembly rotatably coupling the lower end of the attachment member to the prosthetic foot to allow for rotation of the prosthetic foot about a pivot axis extending through the pivot assembly, wherein the pivot assembly is configured to substantially mimic a natural ankle joint The system further includes a sensor assembly coupled to the pivot assembly and configured to detect the rotation of the prosthetic foot about the pivot axis, wherein at least a portion of the sensor assembly is configured to rotate about the pivot axis and is securely positioned along the pivot axis to substantially eliminate other movement.

In another embodiment, a system is disclosed for sensing a rotational movement of a device associated with a limb. The system includes a foot unit and an attachment member having an upper end and a lower end. The system also includes a pivot assembly rotatably coupling the lower end of the attachment member to the foot unit to allow for rotation of the foot unit about an axis extending through the pivot assembly, wherein the pivot assembly is configured to substantially mimic a natural ankle joint. The system further includes a sensor assembly coupled to the pivot assembly and configured to detect the rotation of the foot unit about the axis and to substantially neglect axial and radial movement of the foot unit with respect to the axis.

In another embodiment, a system is disclosed for sensing a rotational movement of a device associated with a lower limb. The system includes a foot means for contacting a ground surface and a means for attaching the foot means to a patient. The system also includes a means for pivotably coupling the foot means to a lower end of the means for attaching to allow for rotation of the foot means about an axis extending through the means for pivotably coupling, wherein the means for pivotably coupling substantially mimics an ankle joint. The system further includes a means for sensing coupled to the means for pivotably coupling, the means for sensing further configured to detect the rotation of the foot means about the axis and to substantially neglect axial and radial movement of the foot means with respect to the axis.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 10 is a table illustrating control signals usable to adjust the ankle angle of a prosthetic or orthotic system according to one embodiment of the invention.

FIG. 12B is a side view of the lower limb prosthesis of FIG. 12A.

FIG. 12C is a cross-sectional view of the lower limb prosthesis of FIG. 12B along plane M-M.

FIG. 16 is a top view of the actuator of FIG. 13.

FIG. 17 is a cross-sectional side view of the actuator of FIG. 13.

DETAILED DESCRIPTION OF THE PREFERRED EMBODIMENTS

Figure 1:
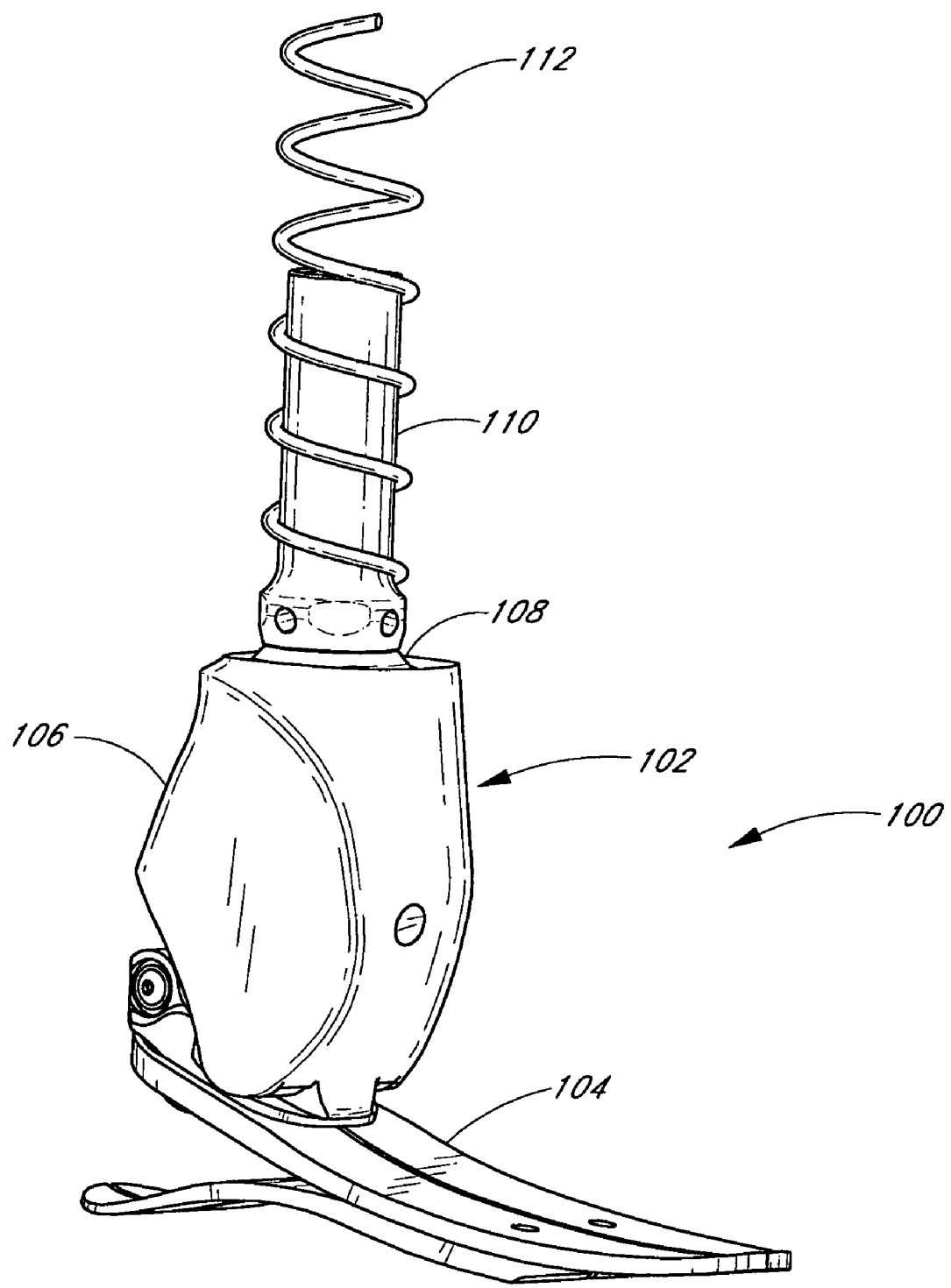
FIG. 1 is a perspective view of a lower limb prosthesis having an ankle-motion-controlled foot unit according to one embodiment of the invention.

Some preferred embodiments of the invention described herein relate generally to prosthetic and orthotic systems and, in particular, to prosthetic and orthotic devices having an ankle-motion-controlled foot. While the description sets forth various embodiment-specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

The features of the system and method will now be described with reference to the drawings summarized above. Throughout the drawings, reference numbers are re-used to indicate correspondence between referenced elements. The drawings, associated descriptions, and specific implementation are provided to illustrate embodiments of the invention and not to limit the scope of the invention.

The terms "prosthetic" and "prosthesis" as used herein are broad terms and are used in their ordinary sense and refer to, without limitation, any system, device or apparatus usable as an artificial substitute or support for a body part.

The term "orthotic" and "orthosis" as used herein are broad terms and are used in their ordinary sense and refer to, without limitation, any system, device or apparatus usable to support, align, prevent, protect, correct deformities of, immobilize, or improve the function of parts of the body, such as joints and/or limbs.

The term "ankle device" as used herein is a broad term and is used in its ordinary sense and relates to any prosthetic, orthotic or ankle-assisting device.

The term "transtibial" as used herein is a broad term and is used in its ordinary sense and relates to without limitation any plane, direction, location, or cross-section that is located at or below a knee joint of a body, including artificial knee joints.

The term "transfemoral" as used herein is a broad term and is used in its ordinary sense and relates to without limitation any plane, direction, location, or cross-section that is located at or above a knee joint of a body, including artificial knee joints.

The term "sagittal" as used herein is a broad term and is used in its ordinary sense and relates to any description, location, or direction relating to, situated in, or being in or near the median plane (i.e., the plane divides the body lengthwise into right and left halves) of the body or any plane parallel or approximately parallel thereto. A "sagittal plane" may also refer to any vertical anterior to posterior plane that passes through the body parallel or approximately parallel to the median plane and that divides the body into equal or unequal right and left sections.

The term "coronal" as used herein is a broad term and is used in its ordinary sense and relates to any description, location, or direction relating to, situated in, or being in or near the plane that passes through the long axis of the body. A "coronal plane" may also refer to any plane that passes vertically or approximately vertically through the body and is perpendicular or approximately perpendicular to the median plane and that divides the body into anterior and posterior sections.

FIG. 1 illustrates one embodiment of a lower limb prosthesis 100 having an ankle-motion-controlled foot with an attachment member. The prosthesis 100 comprises an attachment member, in the form of a lower limb member 102, operatively coupled to a foot unit 104. As used herein, the term "attachment member" is a broad term and is used in its ordinary sense and in a prosthetic foot embodiment relates to, without limitation, any member that attaches either directly or indirectly to the foot unit 104 and is moveable in relation thereto, for example by a pivoting motion, and is used to attach the prosthesis 100 to a stump or intermediate prosthesis. As illustrated, the attachment member may take the form of a lower limb member in an ankle-prosthesis embodiment. In other embodiments, for example an orthotic embodiment, the attachment member may be used to attach to and support a body part, such as with a brace, which also is moveably connected to a second member, such as a foot unit, which would also attach to and support a body part, such as the foot. In one embodiment, the lower limb member 102 is a generally elongated member with a main longitudinal axis that extends in approximately a tibial direction, that is, a direction that extends generally along the axis of a natural tibia bone. For example, FIG. 1 depicts the lower limb member 102 as being a generally vertical orientation.

In another embodiment, the lower limb member 102 may comprise multiple sections. For example, the lower limb member 102 may comprise two elongated sections that extend approximately parallel in a tibial direction and that are connected together. In another embodiment, the lower limb member 102 comprises a two-sided chamber having two substantially symmetrical parts to form a partially enclosed housing. In another embodiment, the lower limb member 102 may comprise a hollow member, such as a tube-like structure. In other embodiments, the lower limb member 102 may comprise elongated flat portions or rounded portions. In yet other embodiments, the structure of the lower limb member 102 is not elongated. For example, the lower limb member 102 may comprise a generally circular, cylindrical, half-circular, dome-shaped, oval or rectangular structure. One example of a possible lower limb member is the ankle module and the structures described in U.S. patent application Ser. No. 10/742,455, filed Dec. 18, 2003, and entitled "PROSTHETIC FOOT WITH ROCKER MEMBER," the entirety of which is hereby incorporated herein by reference and is to be considered as part of this specification.

In one embodiment, the lower limb member 102 is generally formed of a machine metal, such as aluminum, or a carbon fiber material. In other embodiments of the invention, the lower limb member 102 may comprise other materials that are suitable for prosthetic devices. In one embodiment, the lower limb member 102 advantageously has a height between approximately 12 and 15 centimeters. In other embodiments of the invention, the lower limb member 102 may have a height less than 12 centimeters or height greater than 15 centimeters depending on the size of the user and/or the intended use of the prosthesis 100. For example, the lower limb member 102 may have a height of approximately 20 centimeters.

In one embodiment, the prosthesis 100 is configured such that the main longitudinal axis of the lower limb member 102 is substantially perpendicular to a lower surface of the foot unit 104 when the prosthesis 100 is in a resting position. In another embodiment, the lower limb member 102 may be substantially perpendicular to a level ground surface when the foot unit 104 rests on the ground. Such a configuration advantageously provides a user with increased support and/or stability.

As depicted in FIG. 1, the lower limb member 102 further comprises a cover 106. The cover 106 houses and/or protects the inner components of the lower limb member 102. In another embodiment, the cover 106 may be rounded or may be shaped in the form of a natural human leg.

The lower limb member 102 further comprises an attachment portion 108 to facilitate coupling of the lower limb member 102. For example, as depicted in FIG. 1, the attachment portion 108 of the lower limb member 102 couples the prosthesis 100 to a pylon 110. In other embodiments of the invention, the attachment portion 108 may be configured to couple the prosthesis 100 to a stump of an amputee or to another prosthetic device. FIG. 1 also depicts a control wire 112 usable to provide power to and/or communicate control signals to the prosthesis 100.

The foot unit 104 may comprise various types of prosthetic or orthotic feet. As illustrated in FIG. 1, the foot unit 104 incorporates a design described in Applicant's co-pending U.S. patent application Ser. No. 10/642,125, entitled "LOW PROFILE PROSTHETIC FOOT," and filed Aug. 15, 2003 the entirety of which is hereby incorporated by reference and is to be considered as part of this specification. For example, the foot unit 104 may comprise a standard LP VARI-FLEX® unit available from Össur.

In one embodiment, the foot unit 104 is configured to exert a proportional response to weight or impact levels on the foot unit 104. In addition, the foot unit 104 may comprise shock absorption for comfortable loading of the heel and/or for returning expended energy. The foot unit 104 may comprise a full-length toe lever with enhanced flexibility so as to provide a stride length for the prosthetic limb that mimics the stride length of the healthy limb. In addition, as depicted in FIG. 1, the foot unit 104 may comprise a split-toe configuration, which facilitates movement on uneven terrain. The foot unit 104 may also include a cosmesis or a foot cover such as, for example, a standard Flex-Foot cover available from Össur.

Figure 2:
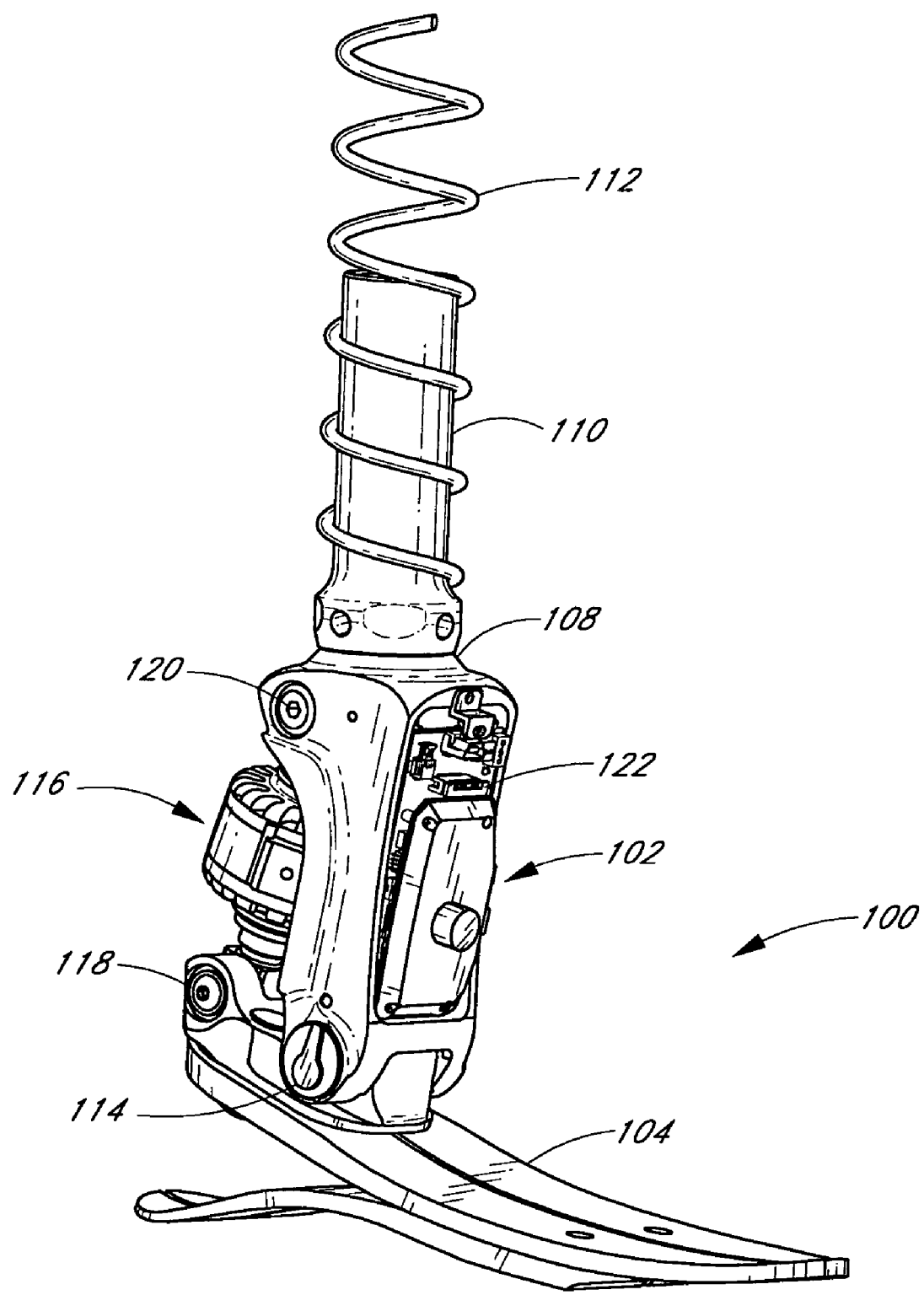
FIG. 2 is a perspective view of the lower limb prosthesis of FIG. 1, wherein a cover is removed to show inner components of the prosthesis.

FIG. 2 depicts the prosthesis 100 with the cover 106 removed. As shown, a lower end of the lower limb member 102 is coupled to the foot unit 104 at a pivot assembly 114. As illustrated, the lower limb member 102 is coupled to an ankle plate of the foot unit 104, which extends generally rearward and upward from a toe portion of the foot unit 104. The pivot assembly 114 allows for angular movement of the foot unit 104 with respect to the lower limb member 102. For example, in one embodiment, the pivot assembly 114 advantageously comprises at least one pivot pin. In other embodiments, the pivot assembly 114 comprises a hinge, a multi-axial configuration, a polycentric configuration, combinations of the same or the like. Preferably, the pivot assembly 114 is located on a portion of the foot unit 104 that is near a natural ankle location of the foot unit 104. In other embodiments of the invention, the pivot assembly 114 may be bolted or otherwise releasably connected to the foot unit 104.

FIG. 2 further depicts the prosthesis 100 having an actuator 116. In one embodiment, the actuator 116 advantageously provides the prosthesis 100 with the necessary energy to execute angular displacements synchronized with the amputee's locomotion. For example, the actuator 116 may cause the foot unit 104 to move similar to a natural human foot. In one embodiment, the lower end of the actuator 116 is coupled to the foot unit 104 at a first attachment point 118. As illustrated, the foot attachment point 118 is advantageously located on the upper surface of the foot unit 104 on a posterior portion thereof. The upper end of the actuator 116 is coupled to the lower limb member 102 at a second attachment point 120. In one embodiment, the linear motion (or extension and contraction) of the actuator 116 controls, or actively adjusts, the angle between the foot unit 104 and the lower limb member 102. FIG. 2 depicts the actuator 116 comprising a double-screw motor, wherein the motor pushes or pulls a posterior portion of the foot unit 104 with respect to the lower limb member 102. In other embodiments, the actuator 116 comprises other mechanisms capable of actively adjusting an angle, or providing for motion between, multiple members. For example, the actuator 116 may comprise a single-screw motor, a piston cylinder-type structure, a servomotor, a stepper motor, a rotary motor, a spring, a fluid actuator, or the like. In yet other embodiments, the actuator 116 may actively adjust in only one direction, the angle between the lower limb member 102 and the foot unit 104. In such an embodiment, the weight of the user may also be used in controlling the angle caused by and/or the movement of the actuator 116.

FIG. 2 illustrates the actuator 116 in a posterior configuration, wherein the actuator 116 is located behind the lower limb member 102. In other embodiments, the actuator 116 may be used in an anterior configuration, wherein the actuator 116 is located in front of the lower limb member 102. In another embodiment of the invention, the actuator 116 comprises an auto adjusting ankle structure and incorporates a design, such as described in U.S. Pat. No. 5,957,981, the entirety of which is hereby incorporated by reference and is to be considered as a part of this specification. The particular configuration or structure may be selected to most closely imitate the movement and location of a natural human ankle joint and to facilitate insertion of the prosthesis 100 into an outer cosmesis.

Furthermore, the actuator 116 is advantageously configured to operate so as to not to emit loud noises, such as intermittent noises, perceptible by the user and/or others. The actuator 116 may also be configured to not operate or adjust if the prosthesis 100 experiences torque, such as in the sagittal plane, that exceeds a certain level. For example, if the torque level exceeds four Newton meters (Nm), the actuator 116 may cease to operate or may issue an alarm.

The actuator 116 may also be substantially enclosed within the cover 106 as shown in FIG. 1 such that the portions of the actuator 116 are not visible and/or exposed to the environment. In another embodiment, the actuator may be at least partially enclosed by the lower limb member 102.

FIG. 2 further depicts control circuitry 122 usable to control the operation of the actuator 116 and/or the foot unit 104. In one embodiment, the control circuitry 122 comprises at least one printed circuit board (PCB). The PCB may further comprise a microprocessor. Software may also reside on the PCB so as to perform signal processing and/or control the movement of the prosthesis 100.

In one embodiment, the prosthesis 100 includes a battery (not shown) that powers the control circuitry 122 and/or the actuator 116. In one embodiment, the battery comprises a rechargeable lithium ion battery that preferably has a power cycle of at least 12 to 16 hours. In yet other embodiments, the power cycle of the battery may be less than 12 hours or may be more than 16 hours. In other embodiments of the invention, the battery comprises a lithium polymer battery, fuel cell technology, or other types of batteries or technology usable to provide power to the prosthesis 100. In yet other embodiments, the battery is removably attached to a rear surface of the lower limb member 102, to other portions of the prosthesis 100, or is located remote the prosthesis 100. In further embodiments, the prosthesis 100 may be connected to an external power source, such as through a wall adapter or car adapter, to recharge the battery.

In one embodiment, the prosthesis 100 is configured to lock in a neutral position, such as the lower limb member 102 being aligned generally vertical relative to a level ground surface when the foot unit 104 is resting on the level ground surface, when the battery is out of power or enters a low power stage. Such locking provides for operational safety, reliability, and/or stability for a user. The prosthesis 100 may also provide a battery status display that alerts the user as to the status (i.e., charge) of the battery. In another embodiment, the prosthesis 100 locks into a substantially neutral position when the motion control functions of the prosthesis 100 are turned off or disabled by a user.

As discussed above, a cosmesis material or other dressings may be used with the prosthesis 100 so as to give the prosthesis 100 a more natural look or shape. In addition, the cosmesis, dressings, or other filler material may be used to prevent contaminants, such as dirt or water, from contacting the components of the prosthesis 100.

Figure 3:
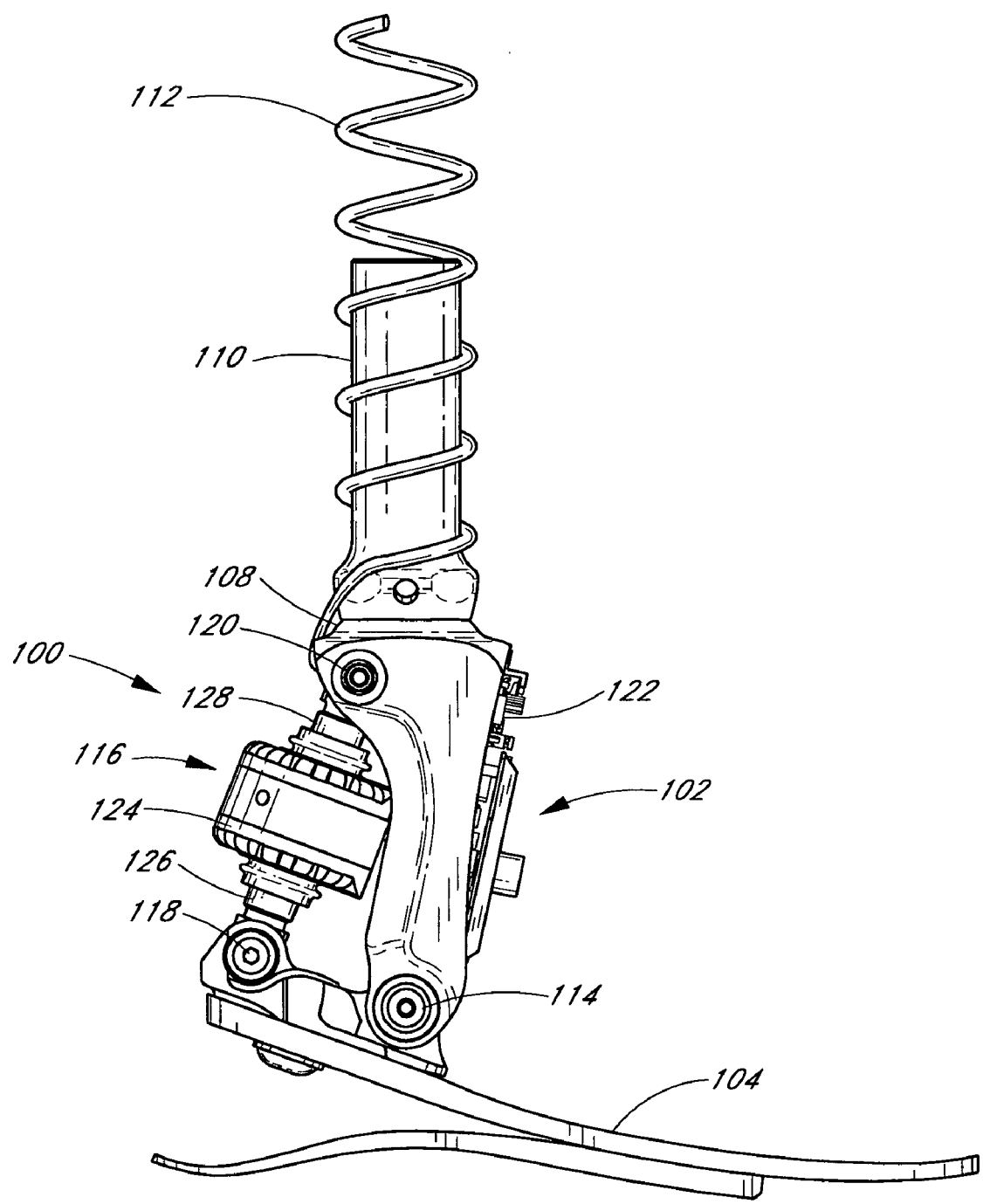
FIG. 3 is a side view of the lower limb prosthesis of FIG. 2.

FIG. 3 depicts a side view of the prosthesis 100 according to one embodiment of the invention. As depicted in FIG. 3, the actuator 116 further comprises a main housing 124, a lower extendable portion 126, and an upper extendable portion 128. The lower extendable portion 126 couples the main housing 124 of the actuator 116 to the foot unit 104 at the first attachment point 118. The upper extendable portion 128 couples the main housing 124 of the actuator 116 to the lower limb member 102 at the second attachment point 120. During operation and active adjustment of the prosthesis 100, the lower extendable portion 126 and/or the upper extendable portion 128 move into and/or out of the main housing 124 of the actuator 116 to adjust an angle between the foot unit 104 and the lower limb member 102.

For example, to increase an angle between the foot unit 104 and the lower limb member 102, the actuator 116 causes the lower extendable portion 126 and/or the upper extendable portion 128 to contract or withdraw into the main housing 124. For example, at least one of the extendable portions 126, 128 may have a threaded surface such that rotation in one direction (e.g., clockwise) causes the extendable portion to withdraw into the main housing 124 of the actuator. In other embodiments, at least one of the extendable portions 126, 128 comprises multiple telescoping pieces such that, upon contraction, one of the multiple pieces of extendable portion contracts into another of the multiple pieces without withdrawing into the main housing 124. Likewise, to decrease an angle between the foot unit 104 and the lower limb member 102, the lower extendable portion 126 and/or the upper extendable portion 128 may extend from the main housing 124.

In embodiments of the invention having an anterior configuration for the actuator 116, extension of the lower extendable portion 126 and/or the upper extendable portion 128 causes an increase in the angle between the lower limb member 102 and the foot unit 104. Likewise, a contraction of the lower extendable portion 126 and/or the upper extendable portion 128 causes a decrease in the angle between the foot unit 104 and the lower limb member 102.

Figure 4:
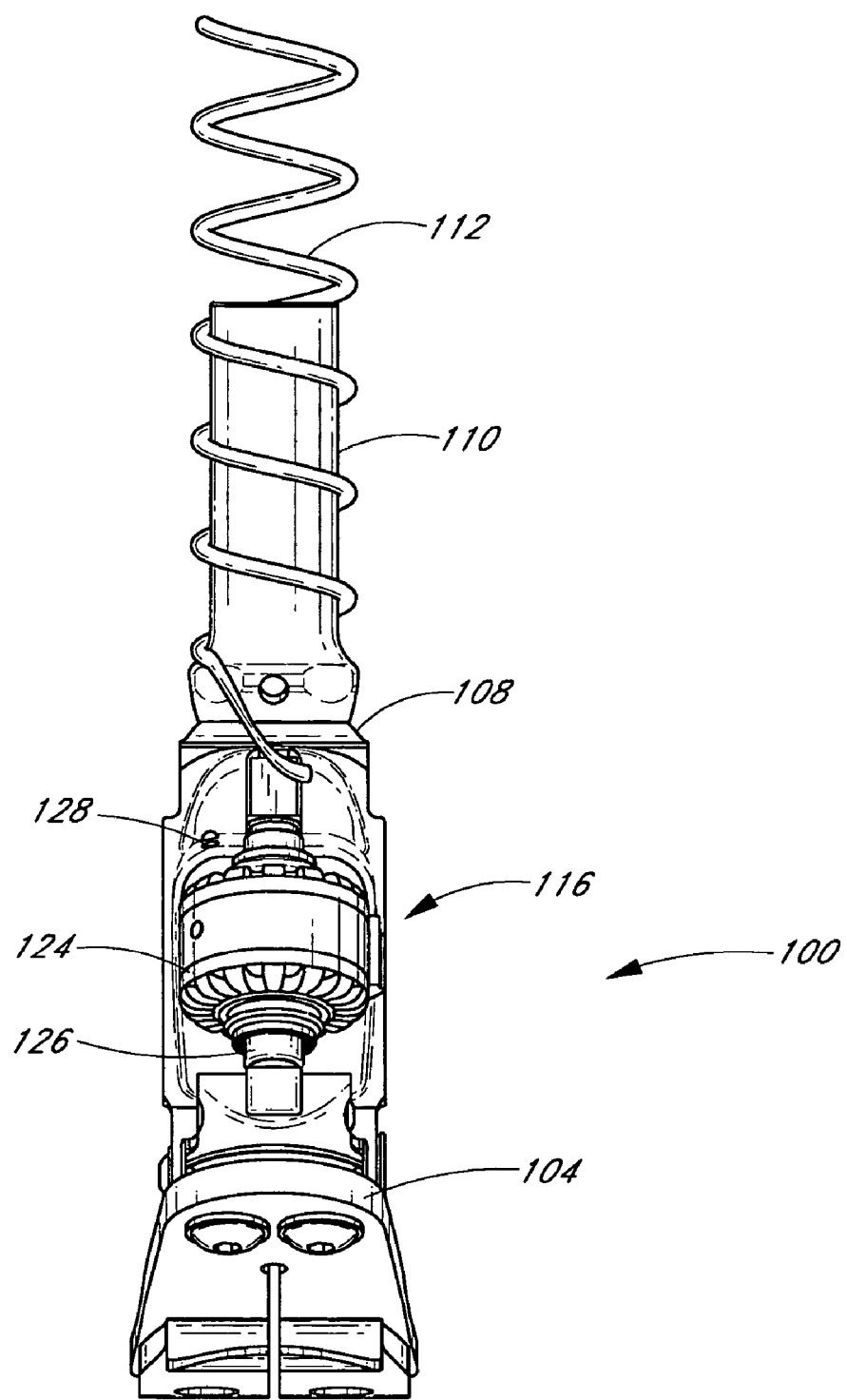
FIG. 4 is a rear view of the lower limb prosthesis of FIG. 2.

FIG. 4 illustrates a rear view of the prosthesis 100 depicted in FIGS. 1-3. In other embodiments of the invention, the cover 106 extends around the posterior portion of the prosthesis 100 to house at least a portion of the actuator 116 such that portions of the actuator 116 are not visible and/or not exposed to the environment.

Figure 5:
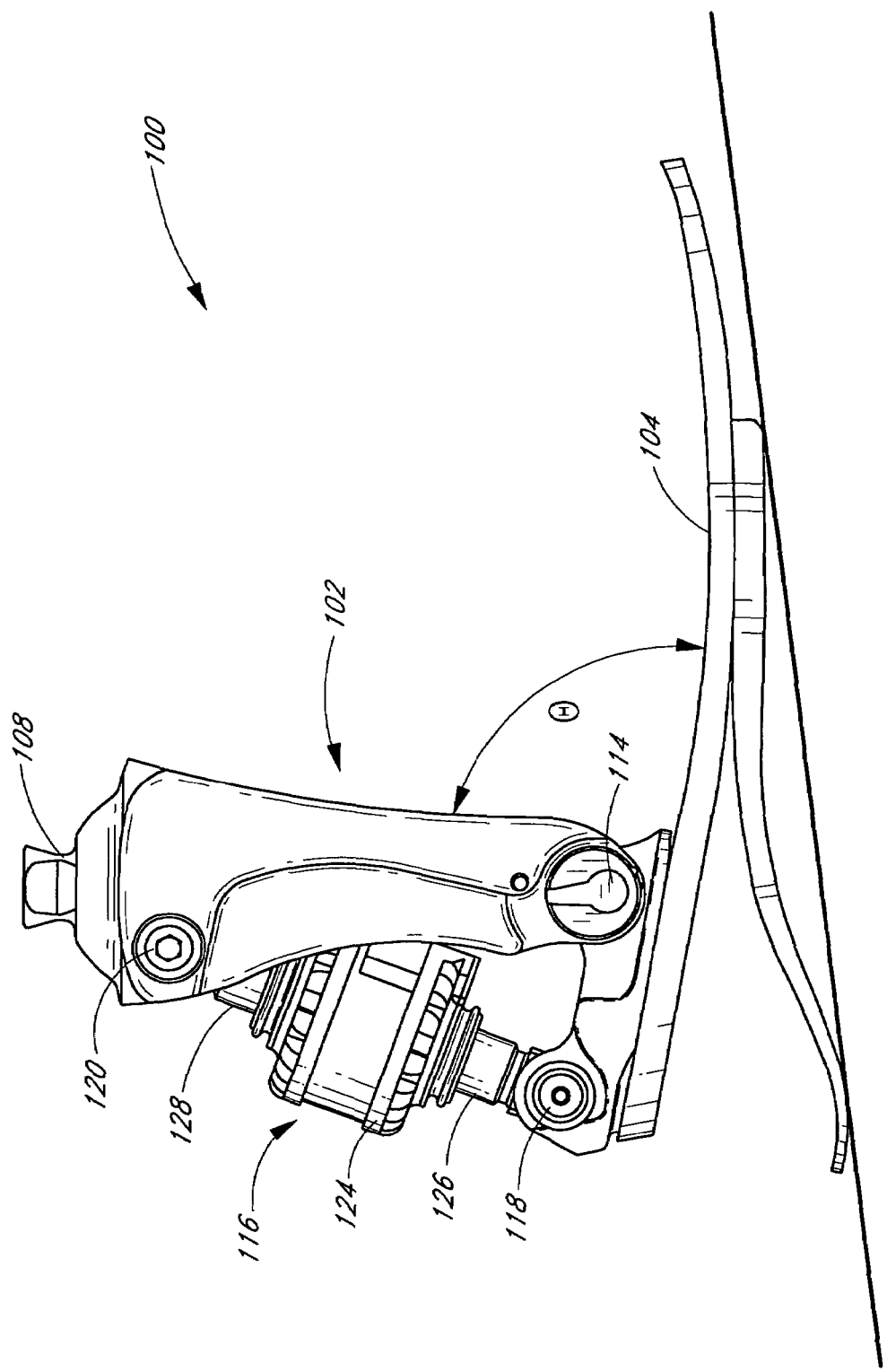
FIG. 5 is a side view of the lower limb prosthesis of FIG. 1 with the cover shown partially removed, wherein the ankle-motion-controlled foot is adjusted to accommodate an incline.
Figure 6:
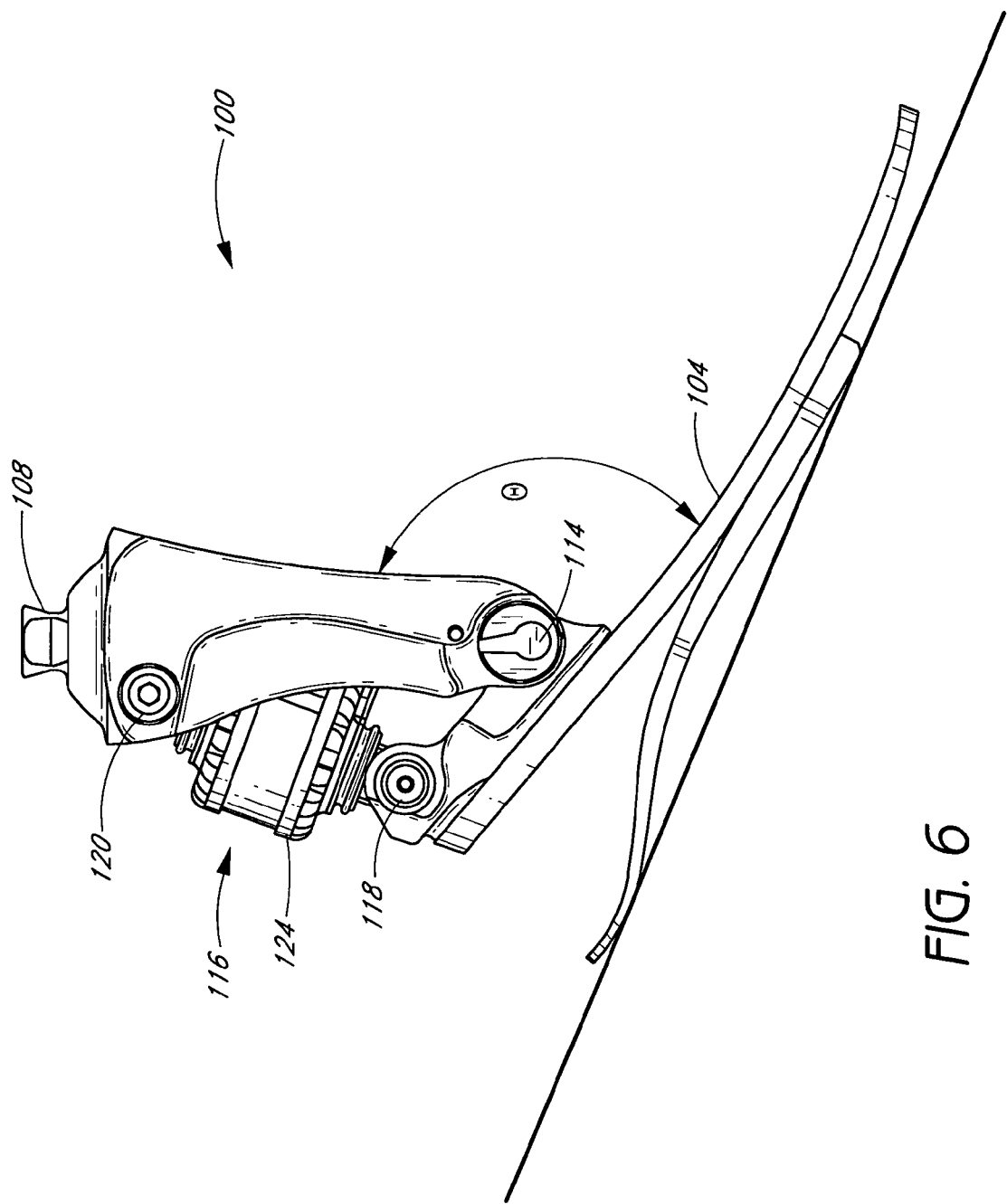
FIG. 6 is a side view of a lower limb prosthesis of FIG. 5, wherein the ankle-motion-controlled foot is adjusted to accommodate a decline.

FIGS. 5 and 6 illustrate one embodiment of the prosthesis 100 as it adjusts to inclines and declines. With reference to FIG. 5, the prosthesis 100 is depicted as adjusting to an incline. In this embodiment, the actuator 116 extends so as to decrease an angle θ between the lower limb member 102 and the foot unit 104 (or "dorsiflexion"). With respect to dorsiflexion, in one embodiment, the angular range of motion of the prosthesis 100 is from about 0 to 10 degrees from the neutral position. Other embodiments may also facilitate exaggerated dorsiflexion during swing phase.

FIG. 6 illustrates the prosthesis 100 as it adjusts to a decline. The actuator 116 extends so as to increase the angle θ between the lower limb member 102 and the foot unit 104 (or "plantarflexion"). With respect to plantarflexion, in one embodiment, the angular range of motion of the prosthesis 100 is from about 0 to 20 degrees from the neutral position. Such plantarflexion mimics natural ankle movement and provides for greater stability to an amputee or a user. In one embodiment, the total range of motion about the ankle pivot axis of the prosthesis 100, including both plantarflexion and dorsiflexion, is approximately 30 degrees or more.

In addition to operating on inclines and declines, the motion-controlled foot of the prosthesis 100 advantageously accommodates different terrain, operates while traveling up and down stairs, and facilitates level ground walking. In addition, the prosthesis 100 may provide for automatic heel height adjustability. Heel height may be measured, in one embodiment, from an ankle portion of the lower limb member 102 to a ground surface when the foot unit 104 is generally flat to the ground. For example, a user may adjust to various heel heights, such as through pressing one or more buttons, such that the prosthesis 100 automatically aligns itself to the appropriate heel height. In one embodiment, the prosthesis 100 includes a plurality of predetermined heel heights. In yet other embodiments, the prosthesis 100 may automatically adjust the heel height without the need for user input.

FIGS. 5 and 6 further illustrate one embodiment of the attachment portion 108. The attachment portion 108 provides alignment between the natural limb of the amputee and the prosthesis 100 and may be configured so as to decrease pressure peaks and shear forces. For example, the attachment portion 108 may be configured to attach to another prosthesis, to the stump of the amputee, or to another component. In one embodiment, the attachment portion 108 comprises a socket connector. The socket connector may be configured to receive a 32 mm-thread component, a male pyramid type coupler, or other components. In other embodiments, the attachment portion 108 may also comprise, or be configured to receive, a female pyramid adapter.

Figure 7:
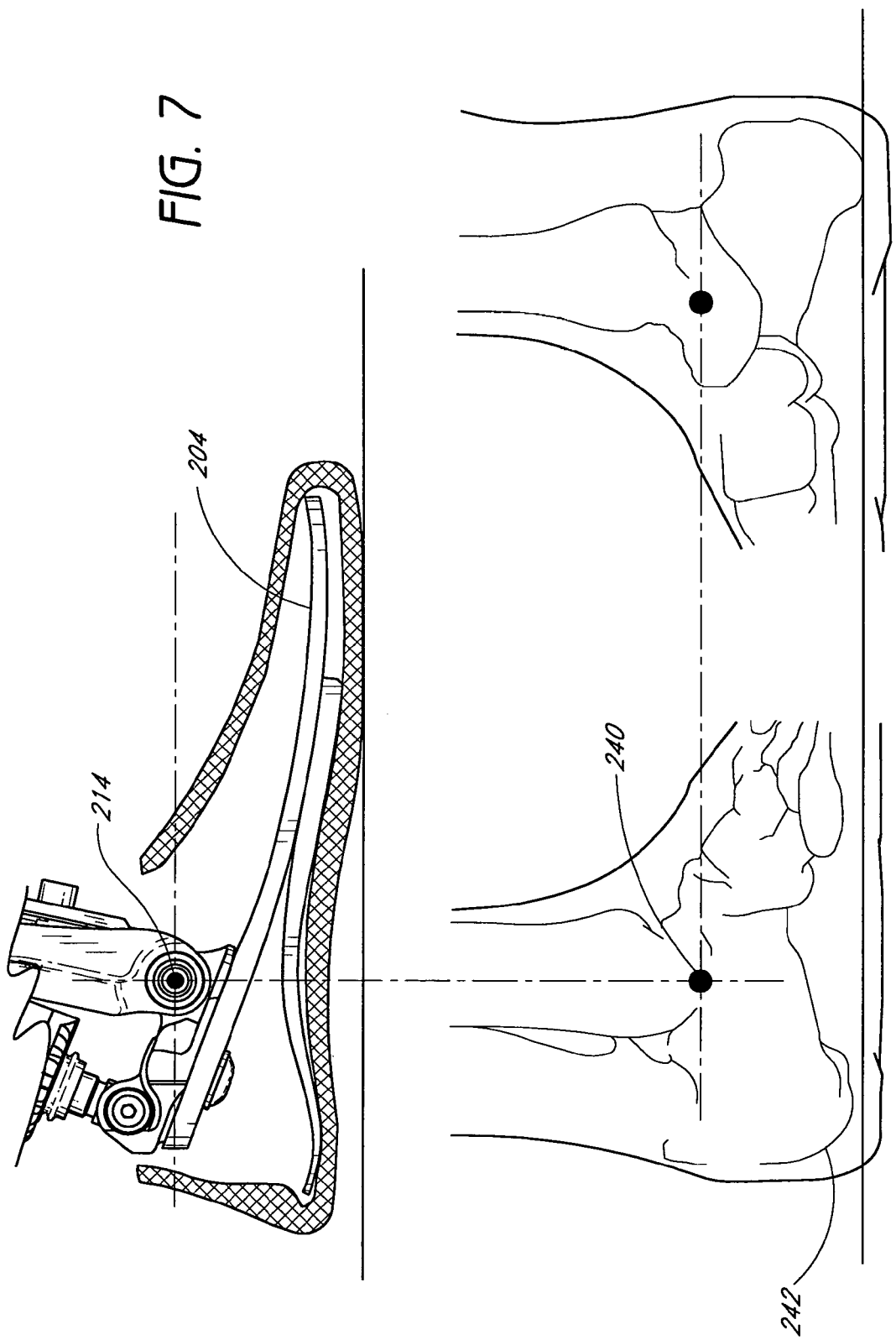
FIG. 7 is a schematic drawing indicating the correlation between an ankle pivot point on an exemplifying embodiment of a prosthetic foot unit with the natural ankle joint of a human foot.

As depicted in FIGS. 5 and 6, the pivot assembly 114 is positioned to mimic a normal human ankle axis. FIG. 7 further illustrates a schematic drawing indicating the correlation between an ankle pivot point on a prosthetic foot unit 204 with the natural human ankle joint of a foot. In particular, the prosthetic foot unit 204 comprises a pivot assembly 214 that corresponds to an ankle joint 240 of a human foot 242. For example, in one embodiment of the invention, the pivot assembly 114 is located near the mechanical ankle center of rotation of the prosthesis 100.

Figure 8:
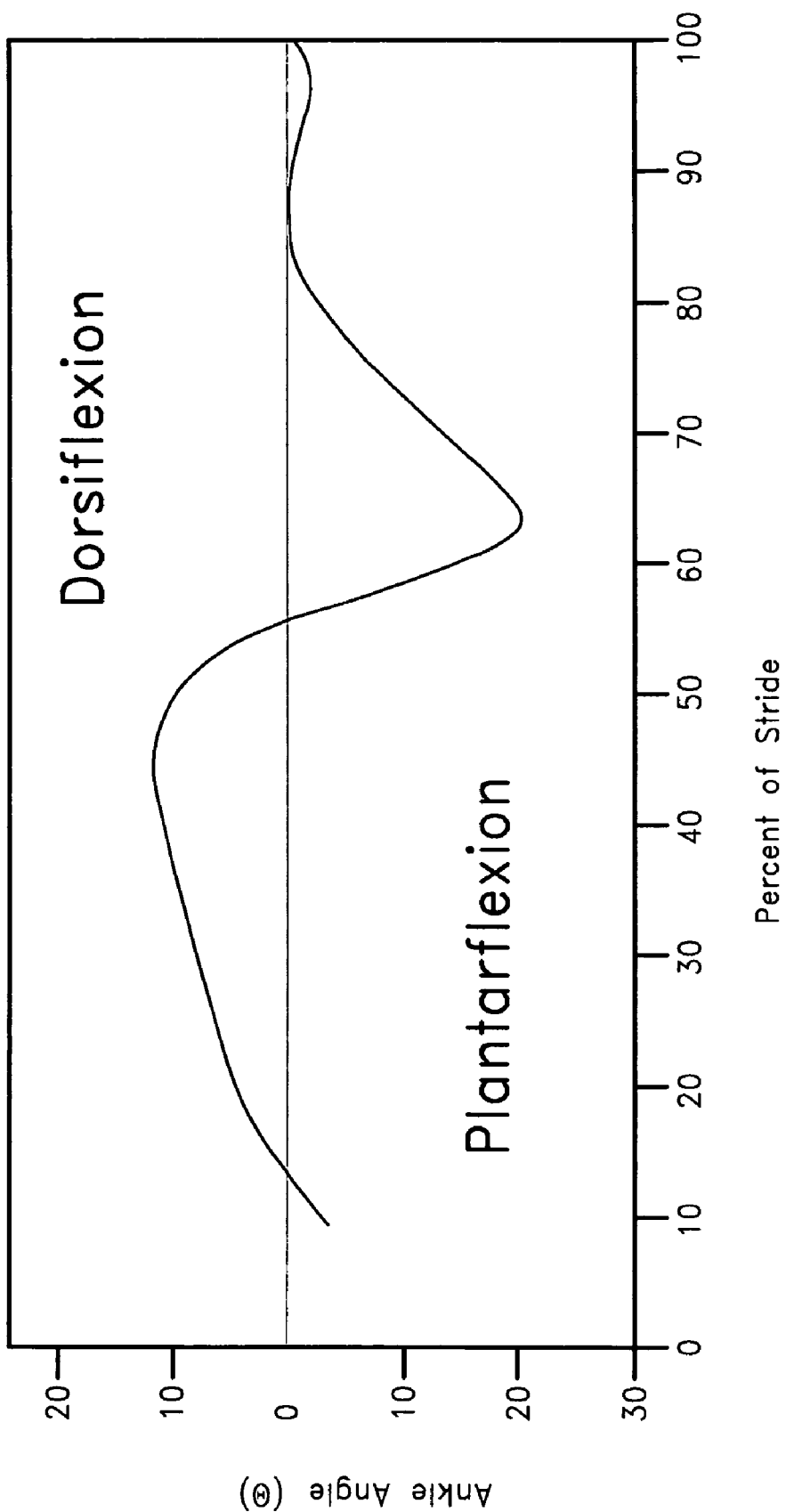
FIG. 8 is a graph depicting the range of ankle motion of an exemplifying embodiment of a prosthetic or orthotic system during one full stride on a level surface.

FIG. 8 illustrates a graph depicting the possible range of ankle motion of an embodiment of the prosthesis 100 during one full stride on a level surface. As shown, the x-axis of the graph represents various points during one full stride of a user (i.e., 0 to 100 percent). The y-axis represents the ankle angle (θ) of the prosthesis 100. During one full stride, the ankle angle (θ) varies from approximately 20 degrees plantarflexion (i.e., neutral position angle +20 degrees) to approximately 10 degrees dorsiflexion (i.e., neutral position angle −20 degrees).

In embodiments as described above, no dampening is provided when adjusting the angular range of motion. In another embodiment of the invention, the prosthesis 100 is configured to provide dampening or passive, soft resistance to changes in the angle between the lower limb member 102 and the foot unit 104. An example of a system for controlling such dampening is disclosed in U.S. Pat. No. 6,443,993, which is hereby incorporated herein by reference and is to be considered as a part of this specification.

For example, when the user is in a standing position, the actuator 116 may provide for increased resistance, or dampening, so as to provide stability to the user. In one embodiment of the invention, dampening of the prosthesis 100 may be provided by hydraulic dampers. In other embodiments of the invention, other components or devices that are known in the art may be used to provide dampening for the prosthesis 100. In addition, in one embodiment of the invention, the dampers may be dynamically controlled, such as through an electronic control system, which is discussed in more detail below. In yet other embodiments, the dampers may be controlled through mechanical and/or fluid-type structures.

It is also recognized that, although the above description has been directed generally to prosthetic systems and devices, the description may also apply to an embodiment of the invention having an orthotic system or device. For example, in one embodiment of the invention, an orthotic system may comprise at least one actuator that actively controls the angle of an orthosis that is used with an injured or debilitated ankle. In addition, the orthotic system may, in addition to the electronic control of the orthotic system, provide for the user's control or natural movement of the injured ankle or leg.

In addition, the above-described systems may be implemented in prosthetic or orthotic systems other than transtibial, or below-the-knee, systems. For example, in one embodiment of the invention, the prosthetic or orthotic system may be used in a transfemoral, or above-the-knee, system, such as is disclosed in U.S. Provisional Application No. 60/569,512, filed May 7, 2004, and entitled "MAGNETORHEOLOGICALLY ACTUATED PROSTHETIC KNEE;" U.S. Provisional Application No. 60/624,986, filed Nov. 3, 2004, and entitled "MAGNETORHEOLOGICALLY ACTUATED PROSTHETIC KNEE;" and U.S. patent application Ser. No. 11/123,870, filed May 6, 2005, and entitled "MAGNETORHEOLOGICALLY ACTUATED PROSTHETIC KNEE;" each of which is hereby incorporated herein by reference in its entirety and is to be considered as part of this specification. For example, the prosthetic or orthotic system may include both a prosthetic or orthotic ankle and/or a prosthetic or orthotic knee.

Figure 9:
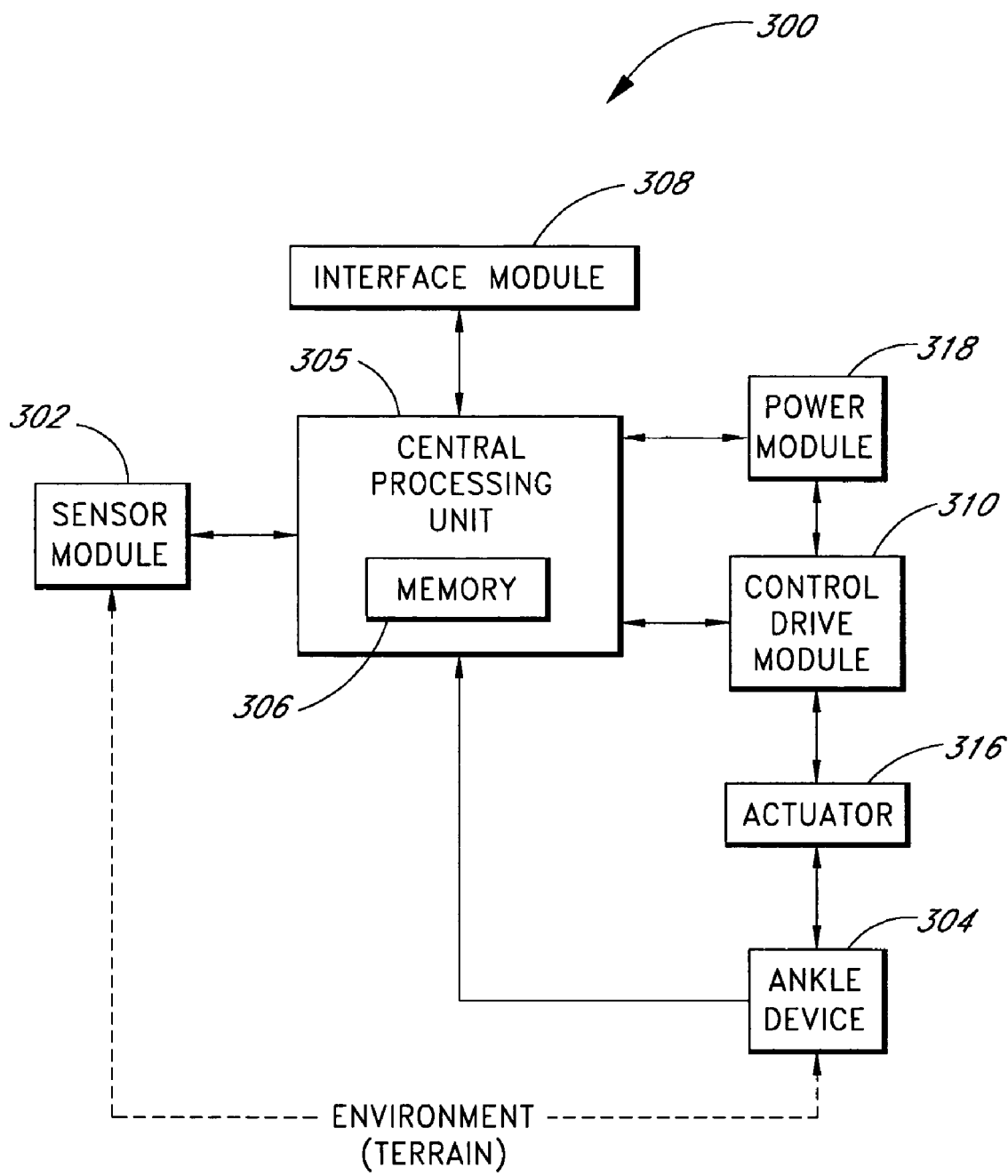
FIG. 9 is a block diagram of an exemplifying embodiment of a control system architecture of a prosthetic or orthotic system having an ankle-motion-controlled foot.

FIG. 9 illustrates a block diagram of one embodiment of a system architecture of a control system 300 for an ankle-motion-controlled foot. In one embodiment of the invention, the control system 300 is usable by the lower limb prosthesis 100 depicted in FIGS. 1-6. In other embodiments of the invention the control system 300 is usable by an orthotic system or a rehabilitation system having an ankle-motion-controlled foot, or other motion-controlled limb. In one embodiment, the control system 300 is based on a distributed processing system wherein the different functions performed by the prosthetic or orthotic system, such as sensing, data processing, and actuation, are performed or controlled by multiple processors that communicate with each other. With reference to FIG. 9, the control system 300 includes a sensor module 302, an ankle device 304 (such as, for example, the prosthesis 100 depicted in FIG. 1), a central processing unit ("CPU") 305, a memory 306, an interface module 308, a control drive module 310, an actuator 316 and a power module 318.

In one embodiment, the control system 300 depicted in FIG. 9 processes data received from the sensing module 302 with the CPU 305. The CPU 305 communicates with the control drive module 310 to control the operation of the actuator 316 so as to mimic natural ankle movement by the ankle device 304. Furthermore, the control system 300 may predict how the ankle device 304 may need to be adjusted in order to accommodate movement by the user. The CPU 305 may also receive commands from a user and/or other device through the interface module 308. The power module 318 provides power to the other components of the control system 300. Each of these components is described in more detail below.

In one embodiment, the sensor module 302 is used to measure variables relating to the ankle device 304, such as the position and/or the movement of the ankle device 304 throughout a gait cycle. In such an embodiment the sensor module 320 is advantageously located on the ankle device 304. For example, the sensor module 302 may be located near a mechanical ankle center of rotation of the ankle device 304, such as the pivot assembly 114 of the prosthesis 100 depicted in FIG. 2. In another embodiment, the sensor module 302 may be located on the user's natural limb that is attached to, or associated with, the ankle device 304. In such an embodiment, the sensors are used to capture information relating to the movement of the natural limb on the user's ankle-device side to adjust the ankle device 304.

In one embodiment, the sensor module 302 advantageously includes a printed circuit board housing, multiple sensors, such as accelerometers, which each measures an acceleration of the ankle device 304 in a different axis. For example, the sensor module 302 may comprise three accelerometers that measure acceleration of the ankle device 304 in three substantially, mutually perpendicular axes. Sensors of the type suitable for the sensor module 302 are available from, for example, Dynastream Innovations, Inc. (Alberta, Canada).

In other embodiments, the sensor module 302 may include one or more other types of sensors in combination with, or in place of, accelerometers. For example, the sensor module 302 may include a gyroscope configured to measure the angular speed of body segments and/or the ankle device 304. In other embodiments, the sensor module 302 includes a plantar pressure sensor configured to measure, for example, the vertical plantar pressure of a specific underfoot area. In yet other embodiments, the sensor module 302 may include one or more of the following: kinematic sensors, single-axis gyroscopes, single- or multi-axis accelerometers, load sensors, flex sensors or myoelectric sensors that may be configured to capture data from the user's natural limb. U.S. Pat. No. 5,955, 667, U.S. Pat. No. 6,301,964, and U.S. Pat. No. 6,513,381, also illustrate examples of sensors that may be used with embodiments of the invention, which patents are herein incorporated by reference in their entireties and are to be considered as part of this specification.

Furthermore, the sensor module 302 may be used to capture information relating to, for example, one or more of the following: the position of the ankle device 304 with respect to the ground; the inclination angle of the ankle device 304; the direction of gravity with respect to the position of the ankle device 304; information that relates to a stride of the user, such as when the ankle device 304 contacts the ground (e.g., "heel strike"), is in mid-stride, or leaves the ground (e.g., "toe-off"), the distance from the ground of the prosthesis 100 at the peak of the swing phase (i.e., the maximum height during the swing phase); the timing of the peak of the swing phase; and the like.

In yet other embodiments, the sensor module 302 is configured to detect gait patterns and/or events. For example, the sensor module 302 may determine whether the user is in a standing/stopped position, is walking on level ground, is ascending and/or descending stairs or sloped surfaces, or the like. In other embodiments, the sensor module 302 is configured to detect or measure the heel height of the ankle device 304 and/or determine a static shank angle in order to detect when the user is in a sitting position.

As depicted in FIG. 9, in one embodiment of the invention, the sensor module 302 is further configured to measure environmental or terrain variables including one or more of the following: the characteristics of the ground surface, the angle of the ground surface, the air temperature and wind resistance. In one embodiment, the measured temperature may be used to calibrate the gain and/or bias of other sensors.

In other embodiments, the sensor module 302 captures information about the movement and/or position of a user's natural limb, such as a healthy leg. In such an embodiment, it may be preferable that when operating on an incline or a decline, the first step of the user be taken with the healthy leg. Such would allow measurements taken from the natural movement of the healthy leg prior to adjusting the ankle device 304. In one embodiment of the invention, the control system 300 detects the gait of the user and adjusts the ankle device 304 accordingly while the ankle device 304 is in a swing phase of the first step. In other embodiments of the invention, there may be a latency period in which the control system 300 requires one or two strides before being able to accurately determine the gait of the user and to adjust the ankle device 304 appropriately.

In one embodiment of the invention, the sensor module 302 has a default sampling rate of 100 hertz (Hz). In other embodiments, the sampling rate may be higher or lower than 100 Hz or may be adjustable by a user, or may be adjusted automatically by software or parameter settings. In addition, the sensor module 302 may provide for synchronization between types of data being sensed or include time stamping. The sensors may also be configured so as to have an angular resolution of approximately 0.5 degrees, allowing for fine adjustments of the ankle device 304.

In one embodiment, the sensor module 302 is configured to power down into a "sleep" mode when sensing is not needed, such as for example, when the user is relaxing while in a sitting or reclining position. In such an embodiment, the sensor module 302 may awake from the sleep state upon movement of the sensor module 302 or upon input from the user. In one embodiment, the sensor module 302 consumes approximately 30 milliamps (mA) when in an "active" mode and approximately 0.1 mA when in a "sleep"mode.

FIG. 9 illustrates the sensor module 302 communicating with the CPU 305. In one embodiment, the sensor module 302 advantageously provides measurement data to the CPU 305 and/or to other components of the control system 300. In one embodiment, the sensor module 302 is coupled to a transmitter, such as, for example, a Bluetooth® transmitter, that transmits the measurements to the CPU 305. In other embodiments, other types of transmitters or wireless technology may be used, such as infrared, WiFi®, or radio frequency (RF) technology. In other embodiments, wired technologies may be used to communicate with the CPU 305.

In one embodiment, the sensor module 302 sends a data string to the CPU 305 that comprises various types of information. For example, the data string may comprise 160 bits and include the following information:

[TS; AccX; AccY; AccZ; GyroX, GyroY, GyroZ, DegX, DegY, FS, M];

wherein TS=Timestamp; AccX=linear acceleration of foot along X axis; AccY=linear acceleration of foot along Y axis; AccZ=linear acceleration of foot along Z axis; GyroX=angular acceleration of foot along X axis; GyroY=angular acceleration of foot along Y axis; GyroZ=angular acceleration of foot along Z axis; DegX=foot inclination angle in coronal plane; DegY=foot inclination angle in sagittal plane; FS=logic state of switches in the ankle device 304; and M=orientation of the sensors. In other embodiments of the invention, other lengths of data strings comprising more or less information may be used.

The CPU 305 advantageously processes data received from other components of the control system 300. In one embodiment of the invention, the CPU 305 processes information relating to the gait of the user, such as information received from the sensor module 302, determines locomotion type (i.e., gait pattern), and/or sends commands to the control drive module 310. For example, the data captured by the sensor module 302 may be used to generate a waveform that portrays information relating to the gait or movement of the user. Subsequent changes to the waveform may be identified by the CPU 305 to predict future movement of the user and to adjust the ankle device 304 accordingly. In one embodiment of the invention, the CPU 305 may detect gait patterns from as slow as 20 steps per minute to as high as 125 steps per minute. In other embodiments of the invention, the CPU 305 may detect gait patterns that are slower than 20 steps per minute or higher than 125 steps per minute.

In one embodiment of the invention, the CPU 305 processes data relating to state transitions according to the following table (TABLE 1). In particular, TABLE 1 shows possible state transitions usable with the control system 300. The first column of TABLE 1 lists possible initial states of the ankle device 304, and the first row lists possible second states of the ankle device 304. The body of TABLE 1 identifies the source of data used by the CPU 305 in controlling, or actively adjusting, the actuator 316 and the ankle device 304 during the transition from a first state to a second state; wherein "N" indicates that no additional data is needed for the state transition; "L" indicates that the CPU 305 uses transition logic to determine the adjustments to the ankle device 304 during the state transition; and "I" indicates the CPU receives data from an interface (e.g., interface module 308, external user interface, electronic interface or the like). Transition logic usable with embodiments of the invention may be developed by one with ordinary skill in the relevant art. Examples of transition logic used in similar systems and methods to embodiments of the present invention are disclosed in U.S. Provisional Application No. 60/572,996, entitled "CONTROL SYSTEM AND METHOD FOR A PROSTHETIC KNEE," filed May 19,2004, and U.S. application Ser. No. 11/077,177, entitled "CONTROL SYSTEM AND METHOD FOR A PROSTHETIC KNEE," filed Mar. 9, 2005,each of which is hereby incorporated herein by reference in its entirety and is to be considered as a part of this specification.

TABLE 1

| TRANSITIONS FROM STATE TO STATE | OFF | HEEL_ HEIGHT_ CAL | SENSOR_ CAL | NEUTRAL | WALK | STAIRS_ UP | STAIRS_ DOWN | RELAX | PANTS |
|---|---|---|---|---|---|---|---|---|---|
| OFF | | N | I | I | I | N | N | N | I | I |
| HEEL_HEIGHT_CAL | L | N | N | L | N | N | N | N | N |
| SENSOR_CAL | L | N | N | L | N | N | N | N | N |
| NEUTRAL | I | I | I | N | L | L | L | L | I |
| WALK | I | N | N | L | N | L | L | N | N |

TABLE 1-continued

| TRANSITIONS FROM STATE TO STATE | OFF | HEEL_HEIGHT_CAL | SENSOR_CAL | NEUTRAL | WALK | STAIRS_UP | STAIRS_DOWN | RELAX | PANTS |
|---|---|---|---|---|---|---|---|---|---|
| STAIRS_UP | I | N | N | L | L | N | L | N | N |
| STAIRS_DOWN | I | N | N | L | L | L | N | N | N |
| RELAX | I | N | N | L | N | N | N | N | I |
| PANTS | I | N | N | I | N | N | N | N | N |

In one embodiment, the above described states in TABLE 1 are predefined states of the ankle device 304. For example, the "OFF" state may indicate that the functions of the ankle device 304 and the actuator 316 are in an off or suspend mode. The "HEEL_HEIGHT_CAL" state relates to the measuring of a heel height from a static sensor angle such as, for example, when the ankle device 304 is not in motion. The "SENSOR_CAL" state relates to surface angle calibration when the user is walking on a level surface. The "NEUTRAL" state relates to when the ankle device 304 is locked in a substantially fixed position. The "WALK" state relates to when the user is walking, such as on a level or sloped surface. "The "STAIRS_UP" and "STAIRS_DOWN" states relate to when the user is walking, respectively, up and down stairs. The "RELAX" state relates to when the user is in a relaxed position. For example, in one embodiment, the "RELAX" state relates to when a user is in a sitting position with the limb having the ankle device 304 crossed over the other limb. In such an embodiment, the control system 300 may cause the ankle device 304 to move into a maximum plantarflexion position to mimic, for example, the natural position and/or look of a healthy foot. The "PANTS" state relates to when a user is putting on pants, trousers, shorts or the like. In such a state, the control system 300 may, in one embodiment, cause the ankle device 304 to move into a maximum plantarflexion position to facilitate putting the clothing on over the ankle device 304.

In other embodiments of the invention, other states are usable with the ankle device 304 in place of, or in combination with, the states identified in TABLE 1. For example, states may be defined that correspond to lying down, cycling, climbing a ladder or the like. Furthermore, in controlling the state transitions, the CPU 305 and/or control system 300 may process or derive data from sources other than those listed in TABLE 1.

In other embodiments, the CPU 305 may perform a variety of other functions. For example, the CPU 305 may use information received from the sensor module 302 to detect stumbling by the user. The CPU 305 may function as a manager of communication between the components of the control system 300. For example, the CPU 305 may act as the master device for a communication bus between multiple components of the control system 300. As illustrated, in one embodiment, the CPU 305 communicates with the power module 318. For example, the CPU 305 may provide power distribution and/or conversion to the other components of the control system 300 and may also monitor battery power or battery life. In addition, the CPU 305 may function so as to temporarily suspend or decrease power to the control system 300 when a user is in a sitting or a standing position. Such control provides for energy conservation during periods of decreased use. The CPU 305 may also process error handling, such as when communication fails between components, an unrecognized signal or waveform is received from the sensor module 302, or when the feedback from the control drive module 310 or the ankle device 304 causes an error or appears corrupt.

In yet other embodiments of the invention, the CPU 305 uses or computes a security factor when analyzing information from the sensor module 302 and/or sending commands to the control drive module 310. For example, the security factor may include a range of values, wherein a higher value indicates a higher degree of certainty associated with a determined locomotion type of the user, and a lower security factor indicates a lower degree of certainty as to the locomotion type of the user. In one embodiment of the invention, adjustments are not made to the ankle device 304 unless the locomotion type of the user is recognized with a security factor above a predetermined threshold value.

In one embodiment, the CPU 305 includes modules that comprise logic embodied in hardware or firmware, or that comprise a collection of software instructions written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors.

FIG. 9 further depicts CPU 305 including a memory 306 for storing instructions and/or data. For example, the memory 306 may store one or more of the following types of data or instructions: an error log for the other components of the control system 300; information regarding gait patterns or curves; information regarding past activity of the user (e.g., number of steps); control parameters and set points; information regarding software debugging or upgrading; preprogrammed algorithms for basic movements of the prosthetic or orthotic system; calibration values and parameters relating to the sensor module 302 or other components; instructions downloaded from an external device; combinations of the same or the like.

The memory 306 may comprise any buffer, computing device, or system capable of storing computer instructions and/or data for access by another computing device or a computer processor. In one embodiment, the memory 306 is a cache that is part of the CPU 305. In other embodiments of the invention, the memory 306 is separate from the CPU 305. In other embodiments of the invention, the memory 306 comprises random access memory (RAM) or may comprise other integrated and accessible memory devices, such as, for example, read-only memory (ROM), programmable ROM (PROM), and electrically erasable programmable ROM (EE- PROM). In another embodiment, the memory 306 comprises a removable memory, such as a memory card, a removable drive, or the like.

In one embodiment, the CPU 305 may also be configured to receive through the interface module 308 user- or activity-specific instructions from a user or from an external device. The CPU 305 may also receive updates to already existing instructions. Furthermore, the CPU 305 may communicate with a personal computer, a personal digital assistant, or the like so as to download or receive operating instructions. Activity-specific instructions may include, for example, data relating to cycling, driving, ascending or descending a ladder, adjustments from walking in snow or sand, or the like.

In one embodiment, the interface module 308 comprises an interface that the user accesses so as to control or manage portions or functions of the prosthetic or orthotic system. In one embodiment, the interface module 308 is a flexible keypad having multiple buttons and/or multiple light emitting diodes (LEDs) usable to receive information from and/or convey information to a user. For example, the LEDs may indicate the status of a battery or may convey a confirmation signal to a user. The interface module 308 may be advantageously located on the ankle device 304. Furthermore, the interface module 308 may comprise a USB connector usable for communication to an external computing device, such as a personal computer.

In a further embodiment, the interface module 308 comprises an on/off switch. In another embodiment, the interface module 308 may receive input regarding the user-controlled heel height or a forced relaxed mode of the prosthetic or orthotic system. In other embodiments, the user may adjust the type of response desired of the prosthesis or enable/disable particular functions of the ankle device 304. The input from the user may be entered directly via the interface module 308, such as through actuating a button, or user input may be received via a remote control.

The interface module 308 may comprise a touch screen, buttons, switches, a vibrator, an alarm, or other input-receiving or output structures or devices that allow a user to send instructions to or receive information from the control system 300. In another embodiment of the invention, the interface module 308 comprises an additional structure, such as a plug, for charging a battery powering the control system 300, such as at home or in a vehicle. In other embodiments of the invention, the interface module 308 may also communicate directly or indirectly with components of the control system 300 other than the CPU 305.

The control drive module 310 is used to translate high-level plans or instructions received from the CPU 305 into low-level control signals to be sent to the actuator 316. In one embodiment, the control drive module 310 comprises a printed circuit board that implements control algorithms and tasks related to the management of the actuator 316. In addition, the control drive module 310 may be used to implement a hardware abstraction layer that translates the decision processes of the CPU 305 to the actual hardware definition of the actuator 316. In another embodiment of the invention, the control drive module 310 may be used to provide feedback to the CPU 305 regarding the position or movement of the actuator 316 or ankle device 304. The control drive module 310 may also be used to adjust the actuator 316 to a new "neutral" setting upon detection by the CPU 305 that the user is traveling on an angled surface.

In one embodiment of the invention, the control drive module 310 is located within the ankle device 304. In other embodiments, the control drive module 310 may be located on the outside of the ankle device 304, such as on a socket, or remote to the ankle device 304.

The actuator 316 provides for the controlled movement of the ankle device 304. In one embodiment, the actuator 316 functions similarly to the actuator 116 described with respect to FIGS. 1-6, which actuator 116 controls the ankle motion of the prosthesis 100. In other embodiments of the invention, the actuator 316 may be configured to control the motion of an orthotic device, such as a brace or other type of support structure.

The ankle device 304 comprises any structural device that is used to mimic the motion of a joint, such as an ankle, and that is controlled, at least in part, by the actuator 316. In particular, the ankle device 304 may comprise a prosthetic device or an orthotic device.

The power module 318 includes one or more sources and/or connectors usable to power the control system 300. In one embodiment, the power module 318 is advantageously portable, and may include, for example, a rechargeable battery, as discussed previously. As illustrated in FIG. 9, the power module 318 communicates with the control drive module 310 and the CPU 305. In other embodiments, the power module 318 communicates with other control system 300 components instead of, or in combination with, the control drive module 310 and the CPU 305. For example, in one embodiment, the power module 318 communicates directly with the sensor module 302. Furthermore, the power module 318 may communicate with the interface module 308 such that a user is capable of directly controlling the power supplied to one or more components of the control system 300.

The components of the control system 300 may communicate with each other through various communication links. FIG. 9 depicts two types of links: primary communication links, which are depicted as solid lines between the components, and secondary communication links, which are depicted as dashed lines. In one embodiment, primary communication links operate on an established protocol. For example, the primary communication links may run between physical components of the control system 300. Secondary communication links, on the other hand, may operate on a different protocol or level than the primary communication links. For example, if a conflict exists between a primary communication link and a secondary communication link, the data from the primary communication link will override the data from the secondary communication link. The secondary communication links are shown in FIG. 9 as being communication channels between the control system 300 and the environment. In other embodiments of the invention, the modules may communicate with each other and/or the environment through other types of communication links or methods. For example, all communication links may operate with the same protocol or on the same level of hierarchy.

It is also contemplated that the components of the control system 300 may be integrated in different forms. For example, the components can be separated into several sub-components or can be separated into more devices that reside at different locations and that communicate with each other, such as through a wired or wireless network. For example, in one embodiment, the modules may communicate through RS232 or serial peripheral interface (SPI) channels. Multiple components may also be combined into a single component. It is also contemplated that the components described herein may be integrated into a fewer number of modules. One module may also be separated into multiple modules.

Although disclosed with reference to particular embodiments, the control system 300 may include more or fewer components than described above. For example, the control system 300 may further include an actuator potentiometer usable to control, or fine-tune, the position of the actuator 316. The user may also use the actuator potentiometer to adjust the heel height of the ankle device 304. In one embodiment, the actuator potentiometer communicates with the CPU 305. In other embodiments, the control system 300 may include a vibrator, a DC jack, fuses, combinations of the same, or the like.

Examples of similar or other control systems and other related structures and methods are disclosed in U.S. patent application Ser. No. 10/463,495, filed Jun. 17, 2003, entitled "ACTUATED LEG PROSTHESIS FOR ABOVE-KNEE AMPUTEES," now published as U.S. Publication No. 2004/0111163;U.S. patent application Ser. No. 10/600,725, filed Jun. 20, 2003,entitled "CONTROL SYSTEM AND METHOD FOR CONTROLLING AN ACTUATED PROSTHESIS," now published as U.S. Publication No. 2004/0049290; U.S. patent application Ser. No. 10/627,503,filed Jul. 25, 2003, entitled "POSITIONING OF LOWER EXTREMITIES ARTIFICIAL PROPRIOCEPTORS," now published as U.S. Publication No. 2004/0088057, U.S. patent application Ser. No. 10/721,764, filed Nov. 25, 2003, entitled "ACTUATED PROSTHESIS FOR AMPUTEES," now published as U.S. Publication No. 2004/0181289; and U.S. patent application Ser. No. 10/715,989," filed Nov. 18, 2003, entitled "INSTRUMENTED PROSTHETIC FOOT," now published as U.S. Publication No. 2005/0107889; each which is herein incorporated by reference in its entirety and is to be considered as part of this specification. In addition, other types of control systems that may be used in embodiments of the present invention are disclosed in U.S. Provisional Application No. 60/551,717, entitled "CONTROL SYSTEM FOR PROSTHETIC KNEE," filed Mar. 10, 2004; U.S. Provisional Application No. 60/569,511, entitled "CONTROL SYSTEM AND METHOD FOR A PROSTHETIC KNEE," filed May 7, 2004;and U.S. Provisional Application No. 60/572,996, entitled "CONTROL SYSTEM AND METHOD FOR A PROSTHETIC KNEE," filed May 19, 2004, which are herein incorporated by reference in their entireties to be considered as part as this specification.

FIG. 10 is a table that depicts possible control signals that may be involved in adjusting the ankle angle of a prosthetic or orthotic device when a user is transitioning between different states, or types of locomotion, according to one embodiment of the invention. In particular, the states listed in a column 402 identify a first state of the user, and the states listed in a row 404 identify a second state of the user, or the state to which the user is transitioning. The remainder of the table identifies possible actions that may be taken by the prosthetic or orthotic device with respect to the ankle angle. "User set point" is the neutral, or default, value that may be set during shoe heel height adjustment. The angles specified are examples of changes to the ankle angle of the prosthetic or orthotic device. For example, when a user is transitioning from a "stance" state to an "ascending stairs" state, the ankle angle may be adjusted to the angle of the stairs, such as for example, −10 degrees (or 10 degrees dorsiflexion). Ankle angles given in the "Incline (up)" and "Decline" columns reflect threshold levels of ankle angle adjustment depending on the angle of the incline.

The following table (TABLE 2) illustrates possible ankle motion strategies for one embodiment of the invention. The first column of TABLE 2 lists different types of locomotion types or gait patterns that may be frequently detected. The second column of TABLE 2 identifies examples of ankle angle adjustment of the prosthetic or orthotic device during the swing phase of each of the identified locomotion types.

TABLE 2

| Locomotion Type/Gait Pattern | Ankle Motion During Swing Phase of Ankle Device |
|---|---|
| Level Ground Walking | Toe clearance during swing |
| Ascending Stairs | Ankle adjusts to dorsiflexion (e.g., 7.5°) |
| Descending Stairs | Ankle adjusts to dorsiflexion (e.g., 5°) |
| Incline (up) | Ankle adjust to dorsiflexion:<br>a) Two incline angle threshold levels (x°, y°)<br>b) Stepwise (2 steps) angle adjustment (z°, w°)<br>Example: If incline angle > x°, ankle will adjust to −z°; if incline angle > y°, ankle will adjust to −w°, wherein x = 2.5° and y = 5°. |
| Decline | Ankle adjusts to plantarflexion:<br>a) Two decline angle threshold levels (x°, y°)<br>b) Stepwise (2 steps) angle adjustment (z°, w°)<br>Example: If decline angle > x°, ankle will adjust to z°; if decline angle > y°, ankle will adjust to w°, wherein x = 2.5° and y = 5°. |
| Sitting/Relaxed | Set Heel Height |
| Adjust Heel Height | Stepless heel height adjustment up to 20° plantarflexion |

Figure 11:
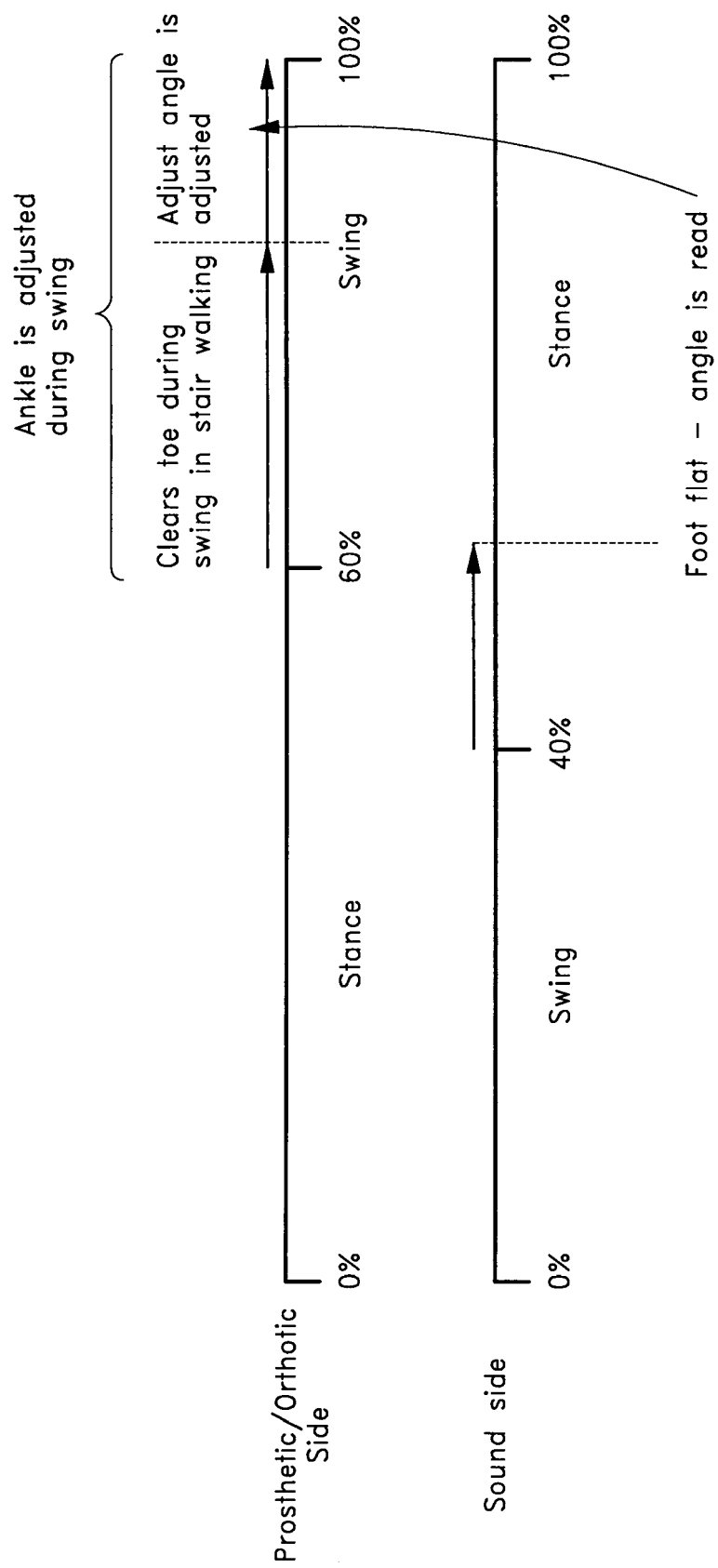
FIG. 11 is a graph depicting an exemplifying embodiment of the relationship between the control of a prosthetic or orthotic system and the motion of a corresponding sound limb.

FIG. 11 depicts a graph that illustrates the interaction and relationship between the control of a prosthetic or orthotic leg and the measurements taken from a healthy, sound leg. In particular, FIG. 11 depicts the movement of a prosthetic or orthotic leg and a healthy leg during one full stride of a user. For example, during approximately the first 60% of the stride, the graph shows the prosthetic or orthotic leg as being in a "stance" position or being planted on a surface, such as the ground. In one embodiment, during the beginning portion of the stance phase the ankle angle of the prosthetic or orthotic leg may decrease (dorsiflexion). Toward the end of the stance phase the ankle angle of the prosthetic or orthotic leg may then increase (plantarflexion) to facilitate natural stride movements. In other embodiments of the invention, the ankle angle of the prosthetic or orthotic leg is not actively adjusted during the stance phase. During a portion of this same period, up to approximately point 40%, the healthy leg may be in a swinging position, wherein the healthy leg is not in contact with the ground. Between the points of approximately 40% and 60%, both legs are in contact with the ground.

From approximately point 60% to 100% (the end of the stride), the prosthetic or orthotic leg is in a swinging position, and the healthy leg is in contact with the ground. The graph in FIG. 11 shows that the ankle angle of the prosthetic or orthotic leg is adjusted during the swing phase. This angle adjustment may be based on previous measurements of the healthy leg during the swing phase of the healthy leg. In one embodiment, during the beginning portion of the swing phase of the prosthetic or orthotic leg, the ankle angle of the prosthetic or orthotic leg may decrease. This allows, for example, a toe portion of the prosthetic or orthotic leg to clear stairs. Toward the latter portion of the swing phase of the prosthetic or orthotic leg, the ankle angle of the prosthetic or orthotic leg may then increase before contacting the ground. In other embodiments, the angle adjustment is based on readings taken by sensors on the prosthetic side.

It is to be understood that FIG. 11 is illustrative of the functioning of one embodiment of the invention under certain conditions. Other embodiments or circumstances may require a longer or shorter stance or swing phase and require other adjustments to the angle of the ankle portion of the prosthetic leg.

Figure 12A:
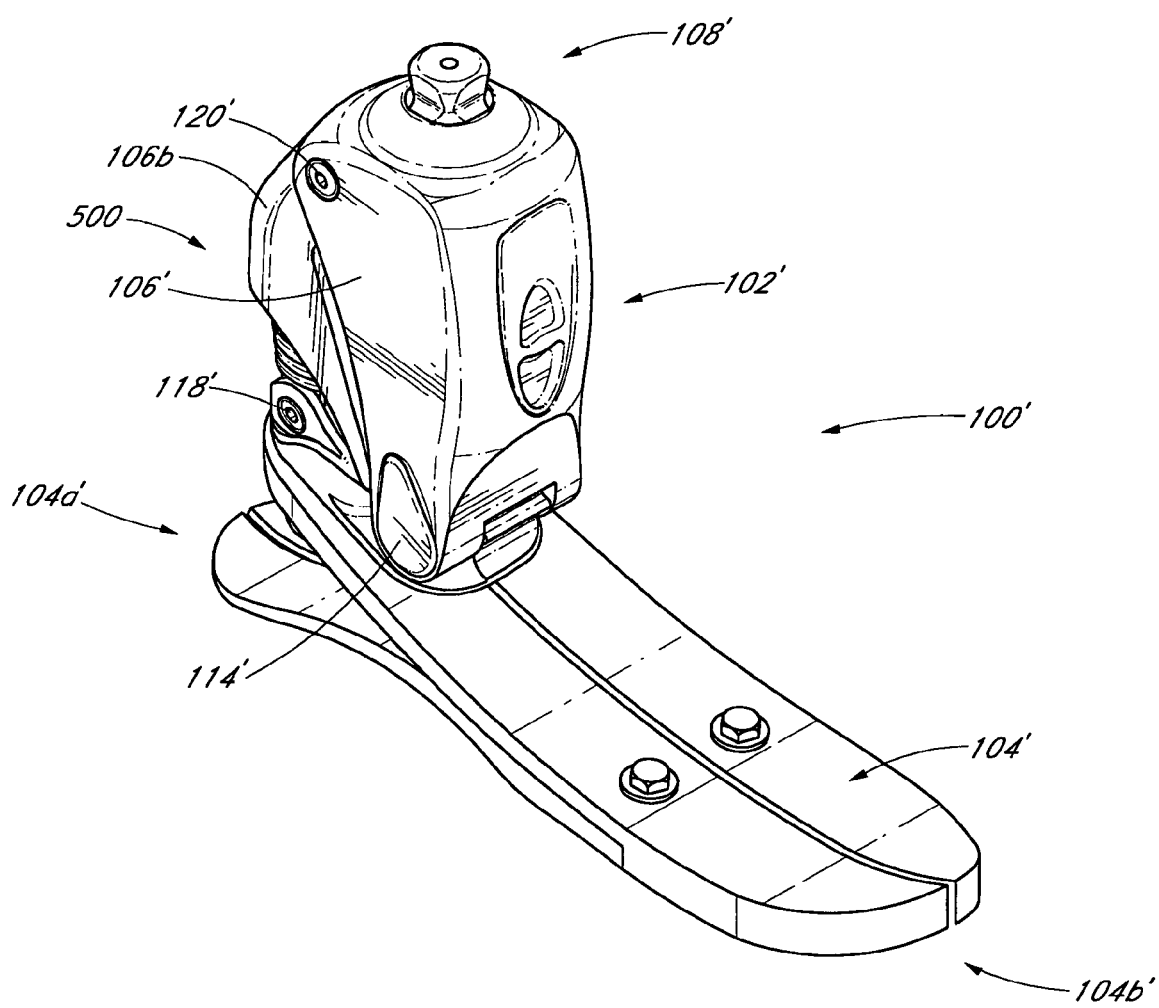
FIG. 12A is a perspective view of another embodiment of a lower limb prosthesis.
Figure 13:
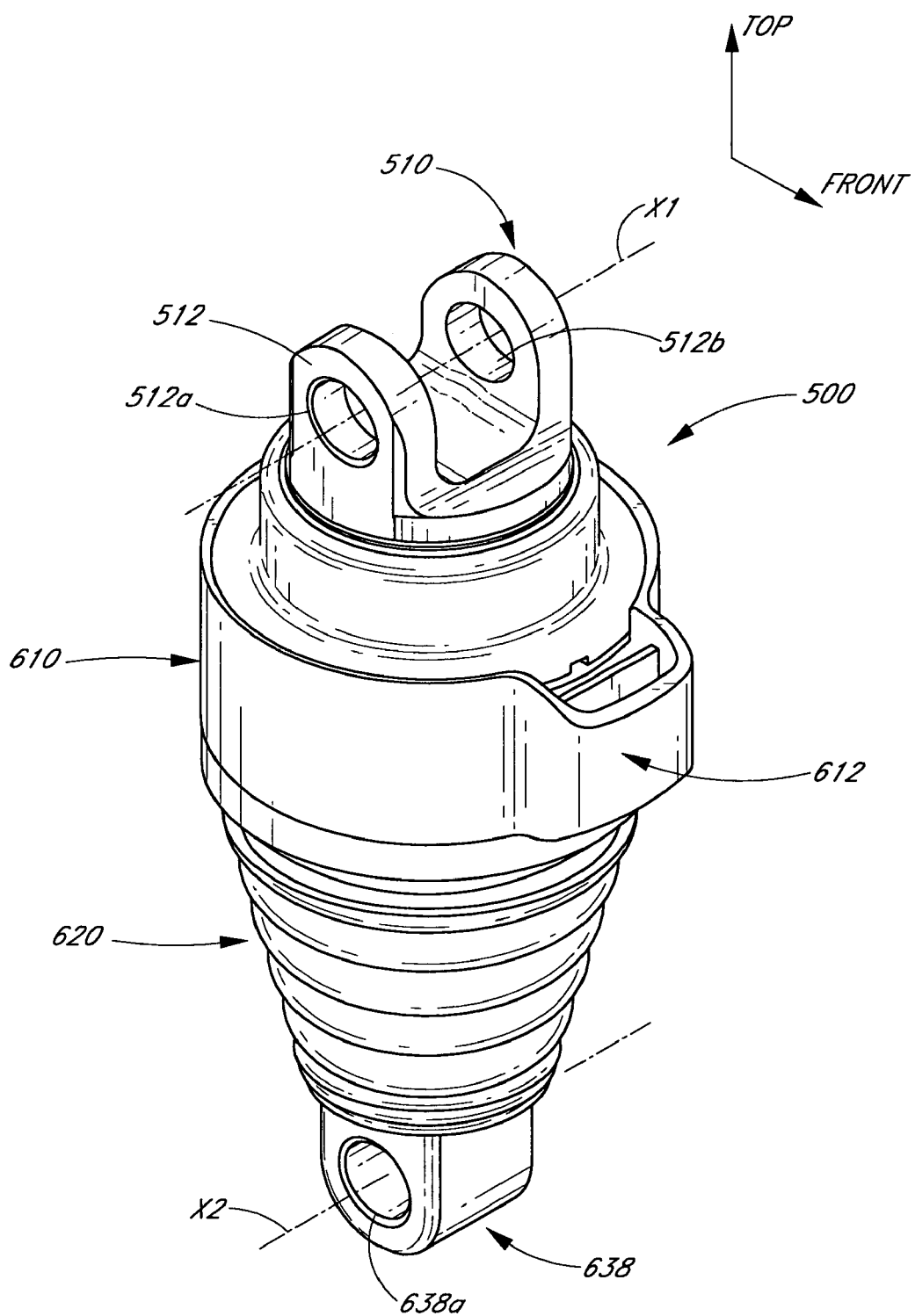
FIG. 13 is a perspective view of one embodiment of an actuator which may be used with the lower limb prosthesis of FIG. 12A.
Figure 15:
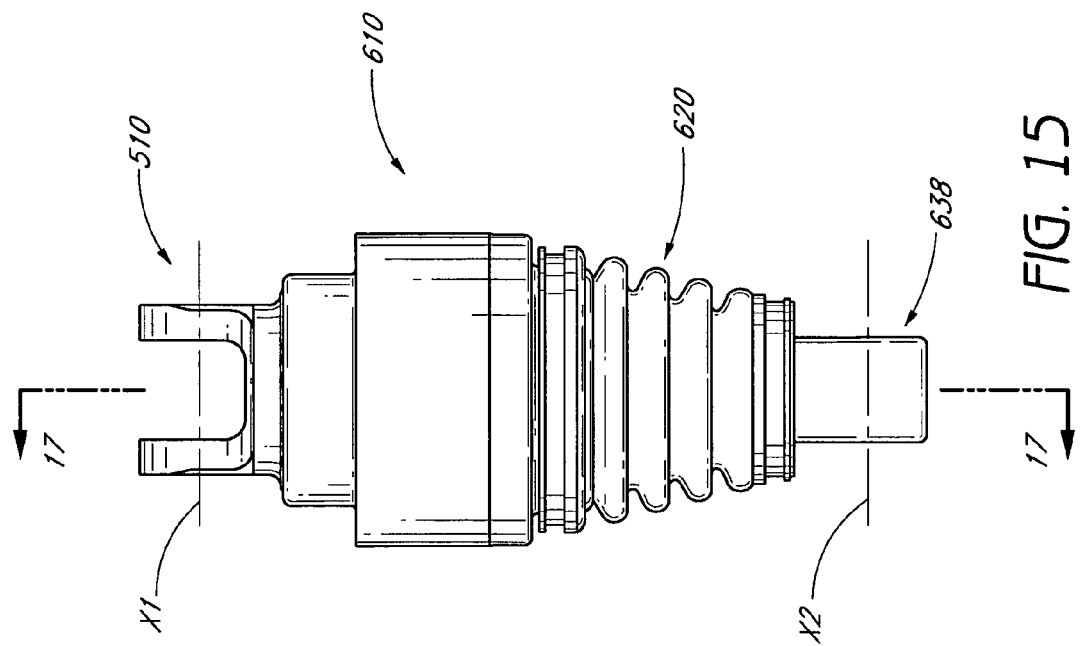
FIG. 15 is a rear view of the actuator of FIG. 13.
Figure 14:
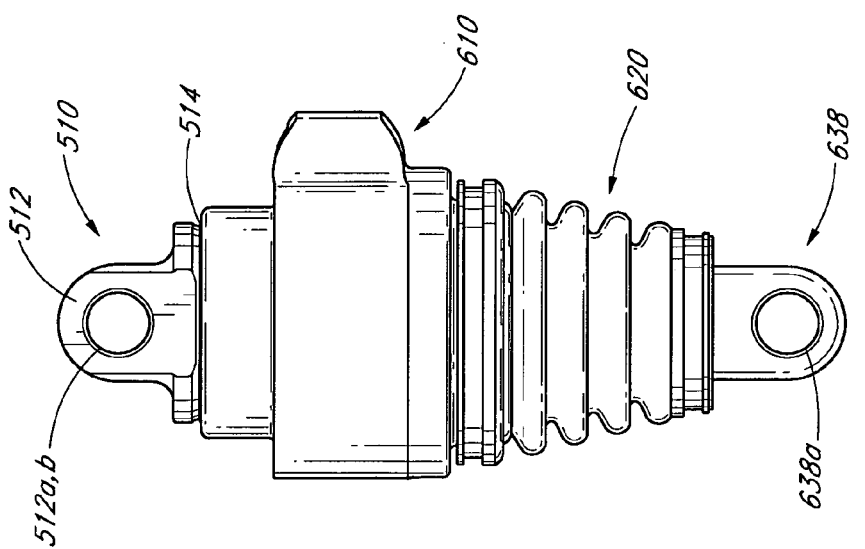
FIG. 14 is a side-view of the actuator of FIG. 13.

FIGS. 12A-12C illustrate another embodiment of a lower limb prosthesis 100' configured to be attached to a human limb. The lower limb prosthesis 100' is similar to the lower limb prosthesis 100 illustrated in FIG. 2, except as noted below. Thus, the reference numerals used to designate the various components of the lower limb prosthesis 100' are identical to those used for identifying the corresponding components of the lower limb prosthesis 100 in FIG. 2, except that a "'" has been added to the reference numerals.

The lower limb prosthesis 100' comprises a first portion 102' coupled to a second portion 104', wherein the portions 102', 104' are moveable relative to each other to mimic a natural human joint. In the illustrated embodiment, the first portion is a lower limb member 102' and the second portion is a prosthetic foot unit 104' coupled to the lower limb member 102' to mimic a natural human ankle joint. The foot unit 104' includes a heel portion 104a' at a rear end of the foot unit 104' and a toe portion 104b' at a front end of the foot unit 104'. In one embodiment, the heel and toe portions 104a', 104b' can be unitary. In another embodiment, the heel and toe portions 104a', 104b' can be separate components fastened to each other via, for example, bolts, screws, adhesives and the like. In the illustrated embodiment, the prosthetic foot unit 104' is an LP VARI-FLEX® prosthetic foot commercially available from Ossur. However, the foot unit 104' can have other configurations or designs. In another embodiment (not shown), the first and second portions can be an upper leg member and a lower leg member, respectively, which are coupled to mimic a natural human knee joint.

As shown in FIG. 12A, the lower limb prosthesis 100' may also comprise a frame 106' extending between the foot unit 104' and the lower limb member 102'. As shown in FIGS. 12A and 12B, an attachment portion 108' of the lower limb member 102' facilitates the coupling of the lower limb member 102' to another member, such as, for example, the pylon 110 depicted in FIGS. 1-4.. In the illustrated embodiment, the attachment portion 108' is a pyramid. Additionally, the lower limb member 102', or support member, couples to the foot unit 104' at its lower end via a pivot assembly 114', which is attached to the prosthetic foot unit 104'. In the illustrated embodiment, the pivot assembly 114' is attached at about the rear ⅓ of the foot unit 104'. However, the pivot assembly 114' can be attached at other locations on the foot unit 104'. Preferably, the pivot assembly 114' mimics a natural human ankle joint. Additionally, a cover 106b' is disposed about an actuator 500 of the lower limb prosthesis 100' to substantially protect the actuator 500 and inhibit the intrusion of foreign matter. In certain embodiments, the lower limb prosthesis 100' may also include a control wire, such as the control wire 112 depicted in FIGS. 1-4, to provide power to and/or communicates control signals to the prosthesis 100'.

With continued reference to FIGS. 12A-12C, the actuator 500 provides the prosthesis 100' with the necessary energy to execute angular displacements synchronized with an amputee's locomotion. The actuator 500 couples the first and second portions 102', 104' of the prosthesis 100' together, which in the illustrated embodiment correspond to the lower limb member 102' and the prosthetic foot unit 104'. As discussed further below, the actuator is configured to adjust an angle between the lower limb member 102' and the foot unit 104'. The actuator 500 couples to the foot unit 104' and the lower limb member 102' at first and second attachment points 118', 120', respectively. In one embodiment, the prosthesis can include control circuitry to control the operation of the actuator 500, such as, for example, the control circuitry 122 depicted in FIGS. 2 and 3.

FIGS. 13-18 illustrate one embodiment of an actuator 500 that may be used with the lower limb prosthesis 100' discussed above. The actuator 500 preferably comprises a stator or top unit 510 having an attachment end 512 and a bottom end 514. In the illustrated embodiment, the attachment end 512 is a C-shaped clamp (see FIG. 15) having a first opening 512a and a second opening 512b aligned along a first axis X1 that extends generally perpendicular to a longitudinal axis Y of the actuator 500. However, the attachment end 512 can have other suitable configurations. The openings 512a, 512b are preferably sized to receive a fastener therethrough, such as a bolt, screw, or pin (not shown), to allow the top unit 510 to be fastened to, for example, the upper end of the lower limb member 102' at the second attachment point 120'.

The bottom end 514 of the top unit 510 preferably has a circumferential wall 514a and a bottom surface 516. In the illustrated embodiment, as shown in FIG. 17, the bottom surface 516 curves from the circumferential wall 514a toward a center of the bottom surface 516. The bottom surface 516 preferably includes a recess portion 518 located generally at the center of the bottom surface 516. The recess portion 518 on the bottom surface 516 of the top unit 510 is preferably sized to receive a ball bearing 522 therein, as further discussed below.

As illustrated in FIG. 17, the circumferential wall 514a includes a protrusion 520 that extends outward from the wall 514a. In one embodiment, the protrusion 520 extends substantially along the entire circumference of the wall 514a. In another embodiment, the protrusion 520 can be a plurality of protrusions positioned at discrete locations about the circumference of the wall 514a.

The actuator 500 also comprises a first elongate member or rotor 530 with a body extending from a top end 530a to a bottom end 530b along a length 532, and having a diameter 534. In one embodiment, the length 532 is between about 25 mm and about 70 mm. In one embodiment, the diameter 534 is between about 12 mm and about 40 mm. More preferably, the diameter 534 is about 17 mm. The rotor 530 has a circumferential flange 536 at the top end 530a, the flange 536 having a diameter greater than the diameter 534 of the body. The top end 530a has an outer surface 537 that curves generally upward from the circumferential flange toward a center 537a of the surface 537. The surface 537 defines a recessed portion 538 generally disposed at the center 537a thereof. The recessed portion 538 is preferably contoured to receive the ball bearing 522 therein, such that the ball bearing 522 couples the top unit 510 to the rotor 530. In one preferred embodiment, the top unit 510 and the rotor 530 couple to each other solely via the ball bearing 522. In the illustrated embodiment, the ball bearing 522 is a single ball bearing. However, other suitable bearings can be used. In one embodiment (not shown) a thrust bearing is disposed between the top unit 510 and the rotor 530. As shown in FIG. 17, the rotor 530 is preferably an elongate nut defining a hollow central portion 539, which defines a wall 539a with threads 540 disposed along at least a portion the length of the wall 539a.

As discussed above, the ball bearing 522 preferably couples the top unit 510 to the first elongate member 530. Preferably, the curvature of the surface 537 of the rotor 530 and the curvature of the bottom surface 516 of the top unit 510 define a gap 541 therebetween. The gap 541 extends preferably circumferentially about the center 537a of the surface 537. In a preferred embodiment, at least one magnet 542 is disposed in the gap 541 and attached to the surface 537 via, for example, an adhesive. In the embodiment illustrated in FIG. 18, a plurality of magnets 542 are disposed about the center 537a of the surface 537. In another embodiment, an annular magnet (not shown) can be disposed on the surface 537, with the annulus of the magnet aligned with the center 537a. The magnets 542 are preferably configured to exert a magnetic force on the top unit 510 and the rotor 530, so that the force draws the top unit 510 and the rotor 530 toward each other.

Figure 18:
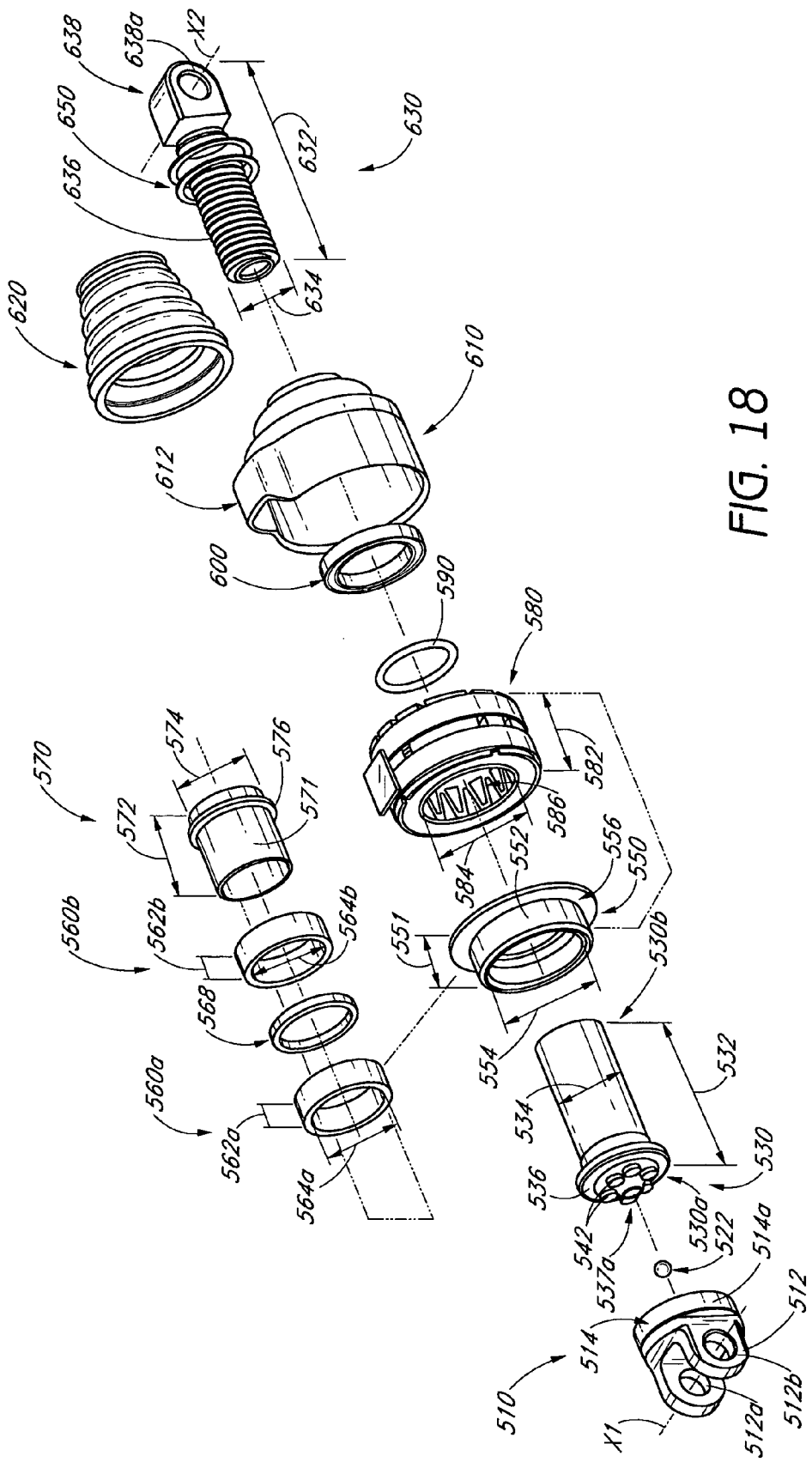
FIG. 18 is an exploded view of the actuator of FIG. 13.

As best seen in FIGS. 17 and 18, the actuator 500 also includes a retainer 550 having a height 551 and a wall 552 defining an inner diameter 554. The retainer 550 includes a flange 556 having an inner portion 556a extending radially inward from the wall 552 and an outer portion 556b extending radially outward from the wall 522, wherein the inner and outer portions 556a, 556b are preferably disposed at a bottom end of the wall 552. Though the illustrated embodiment shows the flange 556 as being continuous around the circumference of the retainer 550, one of ordinary skill in the art will recognize that the flange 556 can instead be a plurality of flange members disposed at discrete locations about the circumference of the retainer 556. The inner diameter 554 of the retainer 550 is sized to receive the rotor 530 and the top unit 510 therein.

In the illustrated embodiment, the inner diameter 554 of the retainer 550 is preferably at least slightly greater than the diameter of the flange 536 of the rotor 530, so that the flange 536 of the rotor 530 does not engage the wall 552 of the retainer 550. Similarly, the inner diameter 554 of the retainer 550 is preferably at least slightly greater than the diameter of at least a portion of the circumferential wall 514a of the top unit 510. The protrusions 520 on the circumferential wall 514a of the top unit 510 preferably engage a portion of the wall 552 of the retainer 550, such that the top unit 510 and the retainer 550 are coupled to each other.

Preferably, rotor 530 rotates about, and translates along, the longitudinal axis Y, as further discussed below. In one embodiment, the rotor 530 remains coupled to the top unit 510 via the ball bearing 522, but selectively moves in and out of contact with the retainer 550 via the inner flange 556a, as further described below. In another embodiment, the rotor 530 moves between contact with the top unit 510, via the ball bearing 522, and contact with the retainer 550 via the inner flange 556a.

As best shown in FIGS. 17 and 18, a first magnet 560a and a second magnet 560b are disposed about a portion of the rotor 530. The first and second magnets 560a, 560b preferably have a height 562a, 562b and an inner diameter 564a, 564b larger than the diameter 534 of the rotor 530, so that the magnets 560a, 560b fit about the rotor 530. In one embodiment, the inner diameters 564a, 564b of the first and second magnets 560a, 560b are between about 12 mm and about 40 mm, and more preferably about 17 mm. In one embodiment, the magnets 560a, 560b are magnetized rings with 24 poles. Additionally, as shown in FIG. 17-18, a spacer 568 is disposed between the first and second magnets 560a, 560b. Preferably, the spacer 568 also has a diameter greater than the diameter 534 of the rotor 530, so that the spacer 568 fits about the rotor 530. Though the illustrated embodiment depicts two magnets 560a, 560b and one spacer 568, one of ordinary skill in the art will recognize that any number of magnets and spacers can be used.

The actuator 500 also comprises a sleeve 570 with a cylindrical body 571 having a length 572 and a diameter 574 such that the sleeve 570 fits about the rotor 530. In one embodiment, the length 572 is between about 10 mm and about 70 mm, and more preferably about 20 mm. The diameter 574 is preferably between about 12 mm and about 40 mm, and more preferably about 17 mm. Preferably, as shown in FIG. 17, the sleeve 570 has an inner diameter greater than the diameter 534 of the first elongate member 530, and has an outer diameter that is smaller than the inner diameter of the first and second magnets 560a, 560b and the spacer 568. Accordingly, the first and second magnets 560a, 560b and the spacer 568 fit about the sleeve 570, which in turn fits about the rotor 530. In a preferred embodiment, the rotor 530, sleeve 570, magnets 560a, 560b are disposed substantially adjacent each other.

As best illustrated in FIGS. 17 and 18, the sleeve 570 also has a lip 576 that extends circumferentially about the sleeve 570. In a preferred embodiment, the lip 576 extends continuously around the sleeve 570 at a radial distance away from a surface of the sleeve 570 substantially equal to a thickness of at least one of the first and second magnets 560a, 560b. The lip 576 is preferably positioned a distance away from a top end of the sleeve 570 so as to support the first and second magnets 560a, 560b and the spacer 568 about the sleeve 570 so that the first and second magnets 560a, 560b and the spacer 568 do not extend past the top end of the sleeve 570.

The actuator 500 also comprises a motor 580. In the illustrated embodiment, the motor 580 has a height 582 and an inner surface 586 with an inner diameter 584, such that the motor 580 can be disposed about the rotor 530. In one embodiment, the motor has a length of between about 10 mm and about 60 mm, and more preferably about 25 mm. the inner diameter 584 of the motor 580 is preferably between about 15 mm and about 50 mm. In a preferred embodiment, the diameter 584 of the motor 580 is about 22 mm. As illustrated in FIG. 17, the motor 580 extends about the rotor 530, such that the sleeve 570, the first and second magnets 560a, 560b and the spacer 568 are disposed between the rotor 530 and the inner diameter 584 of the motor 580. The motor 580 preferably comprises windings configured to rotate the rotor 530 via the magnets 560a, 560b. In the illustrated embodiment, the motor 580 is a stepper motor. However, other suitable motor types can be used. For example, the motor 580 can be a DC motor, a piezo-electric motor, a DC brushless motor, and a servo motor.

As best shown in FIG. 18, the actuator also comprises an o-ring 590 and a roller bearing 600 disposed between the motor 580 and a cover portion 610 having a protruding portion 612. The cover 610 preferably houses the motor 580 therein when the actuator 500 is fully assembled. A bellows 620 is preferably disposed adjacent a bottom end of the cover 610. The bellows 620 advantageously inhibits the entry of foreign particles, such as dust and water, into contact with the motor 580 and a second elongate member 630 of the actuator 500.

The second elongate member 630 extends along a length 632 and has a diameter 634. In the illustrated embodiment, the second elongate member 630 is a screw with threads 636 along a portion of the length 632. In the illustrated embodiment, the screw 630 has an attachment portion 638 at a bottom end thereof with an opening 638a that extends therethrough along an axis X2 generally orthogonal to the longitudinal axis Y of the actuator 500. The opening 638a is preferably sized to receive a fastener therethrough, such as a bolt, a screw or a pin. Accordingly, the attachment portion 638 can be fastened to, for example, the prosthetic foot unit 104' at the first attachment point 118'.

In one preferred embodiment, the threads 636 of the screw 630 are adapted to threadingly engage the threads 540 on the nut 530. Preferably, the threads 636, 540 to the screw 630 and the nut 530, respectively, are designed to be on the boundary of a self-locking coupling. In one preferred embodiment, the threads 636, 540 of the nut 530 and the screw 630, respectively are trapezoidal threads. For example, the threads 636, 540 can be ACME centralized threads with a working diameter of about 14 mm, a pitch of about 2 mm, and about two leads. However, any suitable thread type can be used. In one embodiment, the threads 636, 540 are made of Aluminum Bronze and Stainless Steel. However, other suitable metals and alloys can be used. In one preferred embodiment, the threads 540 in the nut 530 are cut, while the threads 636 in the screw 630 are ground and coated with a coating, such as a permanent oil coating. Advantageously, the thread lengths in the nut 530 are configured to provide minimum friction during operation of the actuator 500, while delivering optimum support and strength to the actuator 500. However, one of ordinary skill in the art will recognize that the threads 540, 636 of the nut 530 and the screw 630 can have other configurations and be made of other materials to provide a desired performance characteristic. For example, the material and coating of the threads, as well as the pitch, working diameter, and number of leads can be varied to provide a different interface friction between the threads 636, 540. In one embodiment, the pitch and configuration of the threads 636, 530 can be chosen so that a load applied (e.g., along the longitudinal axis Y) to the screw 630 and/or nut 530 assembly will not initiate a self-generated movement of the actuator 500. That is, the pitch and configuration of the threads 636, 530 generate a friction force therebetween that is large enough to inhibit the relative rotation of the nut 530 and the screw 630. In another embodiment, the pitch and configuration of the threads 636, 530 can be chosen so that a load applied to the screw 630 and/or nut 530 along the longitudinal axis Y will initiate a self-generated movement of the actuator 500.

As shown in FIG. 17, the screw 630 preferably has a hollow portion 640 extending along a portion of the length 632. Advantageously, the hollow portion 640 reduces the weight of the screw 630, thereby reducing the weight of the actuator 500 as a whole. As shown in FIG. 18, an adoption ring 650 is disposed about the screw 630, wherein the ring 650 couples with the bottom end of the bellows 620.

Advantageously, the actuator 500 has a compact assembly. As discussed above, the motor 580 is disposed about the rotor 530, which is disposed about the elongate member or screw 630. Accordingly, the actuator 500 takes up less space and can have a lower height than other designs. In one preferred embodiment, the actuator 500 has a height of between about 40 mm to about 70 mm in a collapsed configuration, and a height of between about 65 mm to about 130 mm in a fully extended configuration. Additionally, the hollow portion 640 of the screw 630 advantageously reduces the weight of the actuator 500.

In operation, the actuator 500 advantageously minimizes friction between the stator or top unit 510 and the rotor or nut 530. The ball bearing 522 disposed between the top unit 510 and the nut 530 inhibits the generation of a friction force between the top unit 510 and the nut 530, thereby allowing the nut 530 to rotate generally freely relative to the top 510. Additionally, the magnets 542 draw the nut 530 toward the top unit 510, as discussed above. Such a magnetic force lifts the nut 530 from engagement with the inner flange 556a of the retainer 550, thereby inhibiting the generation of friction between the retainer 550 and the nut 530, as further discussed below. In a preferred embodiment, the magnetic force is strong enough to lift the rotor 530 from engagement with the inner flange 556a of the retainer in one desired phase of a gait cycle. In another embodiment, the magnetic force of the magnets 542 is strong enough to lift the rotor 530 from engagement with the inner flange 556a of the retainer 550 in more than one desired phase of a gait cycle.

The actuator 500 can also advantageously be selectively locked during a desired phase of a gait cycle. As illustrated in FIG. 17, the flange 536 of the rotor or nut 530 can engage the inner flange 556a of the retainer 550, generating a friction force between the rotor 530 and the retainer 550 to inhibit the rotation of the rotor 530. Thus, the friction force that is generated is effectively a locking force that locks the actuator 500. In one preferred embodiment, the flanges 536, 556a engage when the actuator 500 is in tension. Additionally, as discussed above, the interaction of the threads 636, 540 of the screw 630 and the nut 530 can also generate a friction force to inhibit the rotation of the screw 630 and the nut 530 relative to each other. Thus, the interaction of the threads 636, 540 also generates a locking force that contributes to the locking of the actuator 500.

Figure 19:
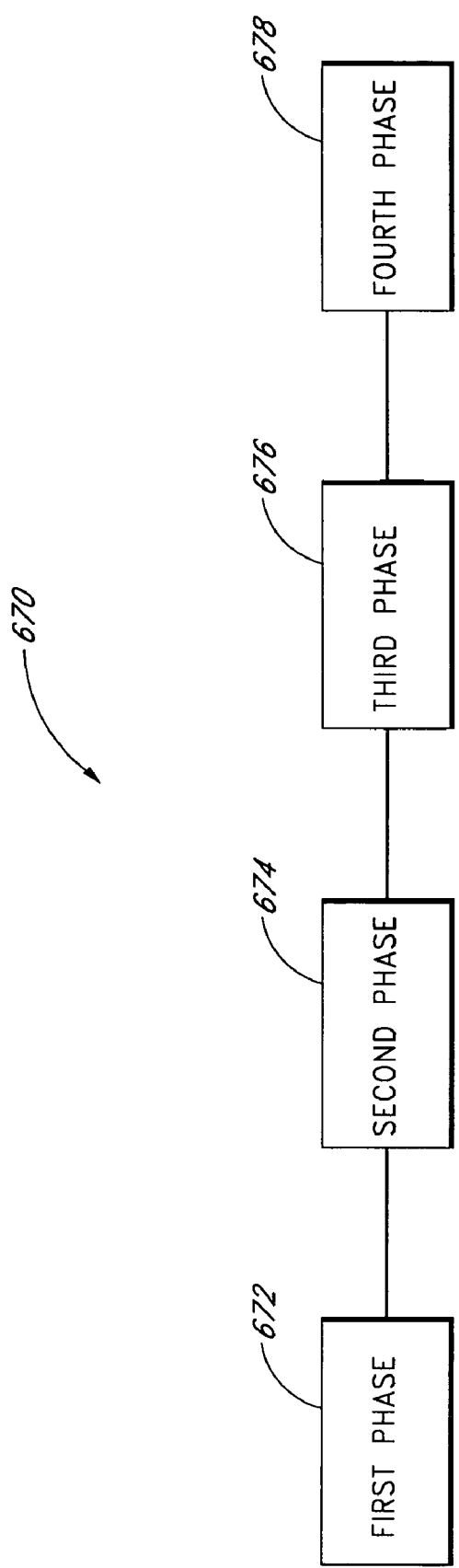
FIG. 19 is a flow chart illustrating different phases of motion of the prosthesis shown in FIG. 12A.

The operation of the actuator 500 during the operation of the lower limb prosthesis 100' by a user will now be described. FIG. 19 illustrates a flow chart showing the different phases of a gait cycle 670 of the lower limb prosthesis 100' illustrated in FIGS. 12A-12C. In a first phase 672 of the gait cycle 670, during heel strike of the foot unit 104', the actuator 500 is initially in a state of compression, wherein the flange 536 on the rotor 530 is displaced relative to the inner flange 556a on the retainer 550.

The state of compression in the first phase arises from the operating relationship between the lower limb member 102' and the prosthetic foot unit 104'. During heel strike, a load is applied on the heel portion 104a' of the foot unit 104' (e.g., due to the weight or locomotion force of the user). Said load applies an upward force on the heel portion 104a' of the foot unit 104', causing the toe portion 104b' to move away from the lower limb member 102' by rotating about the main pivot axis of the pivot assembly 114', which in turn applies a compression force on the second elongate member 630 via the first attachment point 118'. The compression force is transferred from the second elongate member 630 onto the rotor 530, so that the flange 536 of the rotor 530 moves away from the inner flange 556a of the retainer 550.

In one preferred embodiment, the actuator 500 is not actuated during the first phase 672. However, to inhibit the rotation of the rotor 530 relative to the second elongate member 630 during the first phase 672 due to the applied load, the pitch of the threads 540, 636 between the rotor 530 and the second elongated member 630 advantageously generate an interface friction force between the threads 540, 636.

The lower limb prosthesis 100' transitions into a second phase 674 where the foot unit 104' is in a stance phase. During said transition, the actuator 500 transitions from a state of compression to a state of tension, so that a friction force is generated between the flange 536 of the rotor 530 and the inner flange 556a of the retainer 550, as discussed above.

The state of tension in the stance phase is generated by the movement of the lower limb member 102' relative to the prosthetic foot member 104' as the prosthesis 100' transitions into the second phase 674. As the prosthesis 100' moves through the second phase 674, the locomotion of the user (e.g., due to forward movement) applies a load on the lower limb member 102', urging the lower limb member 102' toward the toe portion 104b' of the prosthetic foot unit 104', thus placing a load on the toe portion 104b'. Said load causes a rear portion of the foot unit 104' to move downward, away from the lower limb member 102', which in turn applies a tension force on the second elongate member 630 via the first attachment point 118'. The tension force is transferred from the second elongate member 630 onto the rotor 530, so that the flange 536 of the rotor 530 moves toward, and into engagement with, the inner flange 556a of the retainer 550. As discussed above, said engagement between the flange 536 of the rotor 530 and the inner flange 556a of the retainer 550 generates a friction force to inhibit the rotation of the rotor 530. In one preferred embodiment, the friction force is high enough to act as a brake to prevent the rotation of the rotor 530. Furthermore, in one preferred embodiment, the actuator 500 is not actuated during the second phase 674.

In a third phase 676, the foot unit 104' transitions from a stance phase to a toe-off phase. In toe-off, the toe portion 104b' continues to be under load, as in the second phase. Accordingly, the actuator remains substantially in a state of tension, so that the rotor 530 is inhibited from rotating, as discussed above. In one embodiment, the load on the toe portion 104b' is greater in the third phase than in the second phase of the gait cycle. In one preferred embodiment, the actuator 500 is not actuated during the third phase 676.

In a fourth phase 678, the prosthetic foot unit 104' is in a swing phase between toe-off and heel-strike, wherein the foot 104' is not in contact with a support surface. In the fourth phase 678, the actuator 500 is in a compression position. As discussed above, while in compression the flange 536 on the rotor 530 is separated from the inner flange 556a of the retainer 550, thereby allowing the rotor 530 to rotate generally freely relative to the retainer 550.

The state of compression during the swing phase arises from the operating relationship between the lower limb member 102' and the prosthetic foot unit 104'. During the swing phase, a load is applied to the prosthetic foot unit 104' due to the configuration of the foot unit 104' (e.g., the weight of the foot unit 104'), which pulls the toe portion 104b' downward, away from the lower limb member 102'. The downward force on the toe portion 104b' in turn applies a compression force on the second elongate member 630 via the first attachment point 118'. The compression force is transferred from the second elongate member 630 onto the rotor 530, so that the flange 536 of the rotor 530 moves away from the inner flange 556a of the retainer 550. The rotor 530 is thus able to rotate generally freely relative to the retainer 550. In one embodiment, the movement of the flange 536 of the rotor 530 away from the inner flange 556a of the retainer 550 is facilitated by the magnets 542, which draw the rotor 530 toward the top unit or stator 510 and away from the retainer 550, thus inhibiting the generation of friction during the swing phase.

In one preferred embodiment, the actuator 500 is actuated during the swing phase to adjust the angle between the lower limb member 102' and the prosthetic foot 104'. Advantageously, the ball bearing 522 disposed between the stator 510 and the rotor 530 also inhibit the generation of friction between the rotor 530 and the retainer 550. Therefore, the actuator 500 is actuated while under a light load, which advantageously reduces the wear and tear on the actuator 500, providing for an extended operating life.

As discussed above, in one embodiment the actuator 500 inhibits the rotation of the rotor 530 relative to the second elongate member 630 when in a state of tension. However, one of ordinary skill in the art will recognize that in another embodiment the actuator 500 can be operated to inhibit the rotation of the rotor 530 relative to the second elongate member 630 while in compression. Moreover, in another embodiment the actuator 500 can also be arranged so as to allow for the rotation of the rotor 530 relative to the second elongate member 630 when in a tension position. For example, in one embodiment the magnets 542 can generate a magnetic force sufficient to draw the rotor 530 away from the inner flange 556a of the retainer 550 while the actuator 500 is in a state of tension. Additionally, as discussed above, the actuator 500 is actuated during the swing phase 678 of a gait cycle. However, one of ordinary skill in the art will recognize that the actuator 500 can be actuated during more than one phase of a gait cycle.

Though the operation of the actuator 500 is discussed above in relation to a lower limb prosthesis 100', one of ordinary skill in the art will recognize that the actuator 500 can also be used with an orthotic device to adjust the angle of a first portion and a second portion of the orthotic device. Additionally, the actuator 500, as described in the embodiments above, can advantageously be used to selectively lock the orthotic device during a desired phase of locomotion, as well as to minimize friction between the rotor 530 and the retainer 550 during the actuation of the actuator 500 to facilitate the operation of the orthotic device.

In certain embodiments of the invention, a lower limb prosthesis or orthosis includes at least one sensing device coupled thereto and that is substantially isolated from negative external effects or loads. For example, in certain embodiments, the sensing device is capable of measuring angular movement of a prosthetic foot in a single direction while disregarding or filtering out movement and/or loads of the prosthetic foot in other directions.

Figure 20:
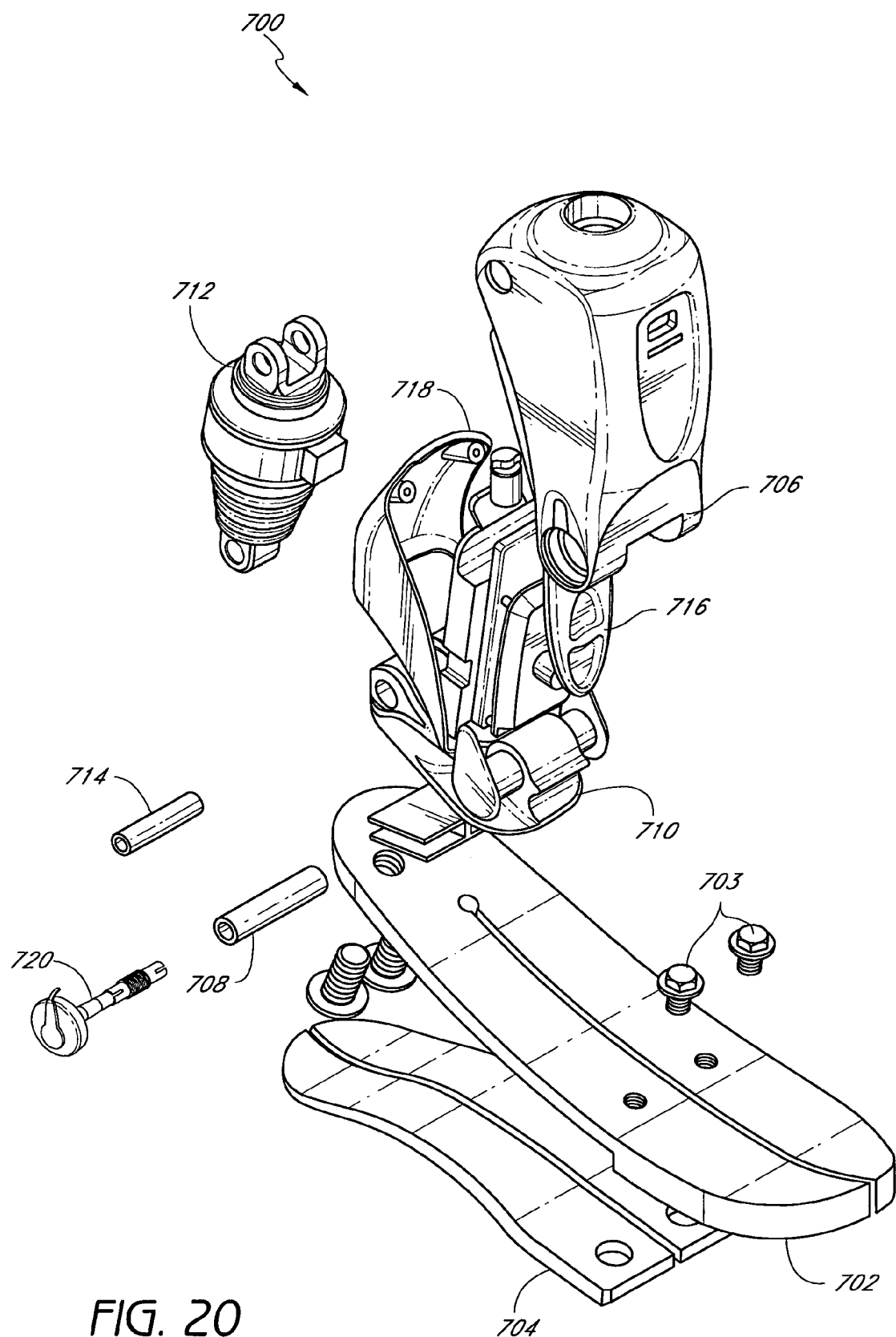
FIG. 20 is a disassembled view of a lower limb prosthesis having an ankle-motion-controlled foot unit according to another embodiment of the invention.

For example, FIG. 20 illustrates a disassembled view of a lower limb prosthesis 700 having an ankle-motion-controlled foot unit. For ease of reference and depiction, certain components, such as certain bolts, washers, bearing plugs and the like, are not shown and described with reference to the illustrated prosthesis 700. A skilled artisan would recognize however, from FIG. 20 and the disclosure herein which components, or equivalents thereof, may be used with the depicted components of the illustrated prosthesis 700.

In certain embodiments, the prosthesis 700 includes at least one sensor assembly that advantageously detects rotation of the foot unit about a single axis and substantially neglects axial and radial movement of the foot unit with respect to the axis. For example, such a sensor assembly may be coupled to and or located near an axis of rotation of the prosthesis 700.

With reference to FIG. 20, the illustrated lower limb prosthesis 700 comprises a foot member 702 connectable by screws 703 to a heel member 704. As shown, the foot member 702 and heel member 704 may comprise a foot unit, such as an LP VARI-FLEX® prosthetic foot commercially available from Össur. In yet other embodiments, the foot member 702 and/or heel member 704 may take on other configurations, or the lower limb prosthesis 700 may operate without a heel member 704.

As illustrated, the foot member 702 is configured to rotatably attach to a main frame 706, or attachment member, about a main pivot pin 708 extending through a base part 710. In certain embodiments, the main pivot pin 708 and the base part 710 form a pivot assembly that is configured to substantially mimic the natural motion of a healthy human ankle. For example, the main pivot pin 708 may allow for dorsiflexion and plantarflexion of the foot member 702, as is described in more detail previously with respect to the prosthesis 100 of FIGS. 1-6.

The prosthesis 700 further includes an actuator 712 operatively coupled to the foot member 702 through the base part 710. In particular, the actuator 712 couples to a lower pin 714 that allows for rotation of a bottom portion of the actuator 712 with respect to the base part 710 secured to a top, rear portion of the foot member 702. In certain embodiments, the actuator 712 is advantageously capable of adjusting at least one angle between the main frame 706 and the foot member 702, such that the foot member 702 rotates about the main pivot pin 708 of the pivot assembly. In certain embodiments, the actuator 712 comprises any one of the various types of actuators disclosed herein and is capable adjusting the angle between the main frame 706 and the foot member 702 based on one or more signals received from an electronic control system.

As shown in FIG. 20, the lower limb prosthesis 700 optionally further includes a keypad 716 to receive user input and a rear cover 718 that partially covers the actuator 712. The prosthesis 700 may also include other devices and/or couplings to facilitate attachment of the prosthesis 700 to a limb, such as a stump, of an amputee.

The illustrated lower limb prosthesis 700 further includes a sensor assembly 720 configured to couple to and extend through the base part 710 of the pivot assembly. In certain embodiments, the sensor assembly 720 is configured to measure movement of at least one portion of the prosthesis 700 in at least one direction. In certain preferred embodiments, the sensor assembly 720 is configured and positioned to measure movement of a portion of the prosthesis 700 in a single direction.

For example, as illustrated in FIG. 20, at least a portion of the sensor assembly 720 is positioned within the main pivot pin 708 and extends along an axis (e.g., a pivot axis) substantially perpendicular to a longitudinal, or vertical, axis of the main frame 706. The illustrated sensor assembly 720 is capable of detecting, or measuring, rotation of the foot member 702 about the axis of the main pivot pin 708. Furthermore, in certain embodiments, the sensor assembly 720 is secured to the pivot assembly of the prosthesis 700 such that the sensor measurements are not affected by loads or forces in directions other than rotation about the main pivot pin 708. For example, in certain embodiments, axial or radial movements with respect to the axis of the main pivot pin 708 do not affect the measurements of the sensor assembly 720.

Figure 21:
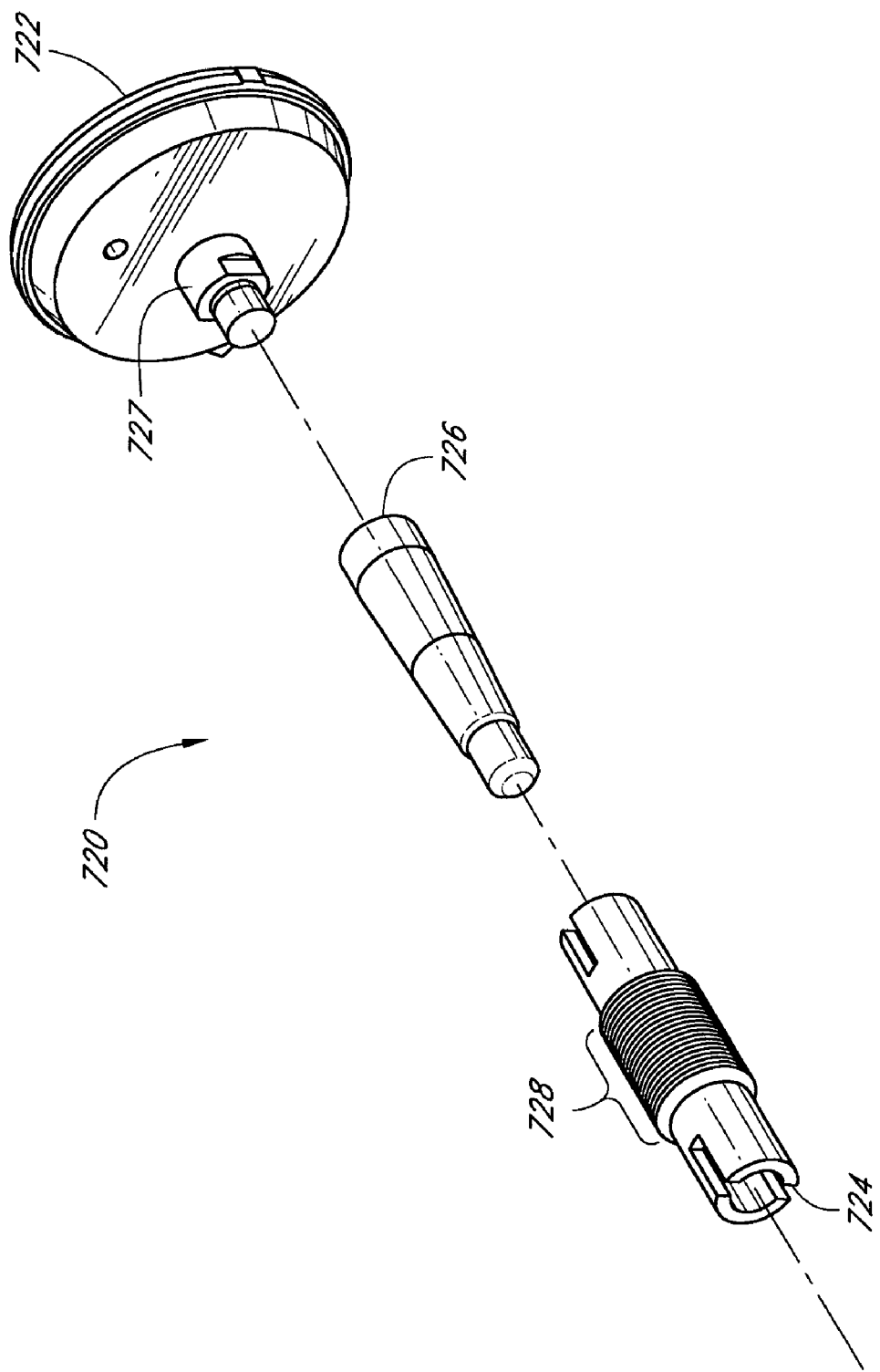
FIG. 21 is a disassembled view of a sensor assembly usable with the lower limb prosthesis of FIG. 20.

FIG. 21 illustrates a disassembled view showing further details of the components of the sensor assembly 720 of FIG. 20. As shown, the sensor assembly 720 includes a displacement measurement sensor 722 coupled to an elongated bellow portion 724 through an extender portion 726. In certain embodiments, relative rotation of the foot member 702 with respect to the main frame 706 is measured by the displacement measurement sensor 722.

Measurements of such rotation may be performed by the sensor assembly 720 in several ways. In certain embodiments, the main pivot pin 708 is rigidly attached to the base part 710, and the elongated bellow portion 724 is positioned at least partially within the main pivot pin 708. In such embodiments, relative movement of the foot member 702 (and attached base part 710) with respect to the main frame 706 causes relative rotation between the elongated bellow portion 724 (and attached extender portion 726) with respect to the displacement measurement sensor 722. For instance, rotation of the foot member 702 may cause rotation of the elongated bellow portion 724 with respect to the displacement measurement sensor 722, which may be fixed with respect to the main frame 706. In other embodiments, rotation of the foot member 702 may cause rotation of the displacement measurement sensor 722 with respect to the elongated bellow portion 722, which may be fixed with respect to the main frame 706.

In certain embodiments, the displacement measurement sensor 722 comprises a potentiometer, such as, for example, a linear or logarithmic potentiometer. In such embodiments, rotation of the elongated bellow portion 724 causes a corresponding rotation of the extender portion 726 and a rotatable input 727 of the potentiometer. In yet other embodiments, other types of displacement measurement sensors may be used, such as, for example, rotational position transducers, optical or mechanical encoders, combinations of the same or the like, to measure movement and/or rotation of a component of the prosthesis 700.

As illustrated in FIG. 21, the elongated bellow portion 724 further includes a plurality of ridges 728 around an outside surface of the bellow portion 724. In certain embodiments, the ridges 728 advantageously eliminate or substantially reduce the effects of axial (e.g., along the axis of the bellow portion 724) and/or radial (e.g., a direction perpendicular to the axis of the bellow portion 724) movements and/or loads on measurements by the displacement measurement sensor 722. For instance, at least some of the ridges 728 may be located within a component housing at least a portion of the elongated bellow portion 724. In certain preferred embodiments, such a component may include the main pivot pin 708 depicted in FIG. 20. In such embodiments, the ridges 728 may advantageously isolate movement of the elongated bellow portion 724 to rotation about the axis of the elongated bellow portion 724 and the main pivot pin 708.

In yet other embodiments, the elongated bellow portion 724 may include a plurality of grooves or other surface features that isolate movement of the elongated bellow portion 724 to a single direction. In yet other embodiments, the sensor assembly 720 may function without the extender portion 726 or the ridges 728. For example, the sensor assembly 720 may include a flexible compression membrane that couples the displacement measurement sensor 722 to the main pivot pin 708 and that absorbs unwanted movement (e.g., axial and/or radial movement).

Although the sensor assembly 720 has been described with reference to particular embodiments, other configurations for the sensor assembly 702 may be used with the prosthesis 700. For example, the main pivot pin 708 may be rigidly attached to the main frame 706. In such embodiments, either the displacement sensor 722 or the elongated bellow portion 724 may also be affixed to the main frame 706 such that relative movement of the foot member 702 with respect to the main frame 706 is detected by the displacement measurement sensor 722.

In yet other embodiments of the invention, the prosthesis 700 may include other types of sensor assemblies usable to detect movement of at least one component of the prosthesis 700. For example, the prosthesis 700 may comprise a ball joint assembly that has its movement constrained in at least one direction by geometric constraints surrounding the ball joint, which constraints may include, for example, one or more pins or flat surfaces that engage one or more surfaces of the ball joint. In yet other embodiments, the sensor assembly 720 may include a flexible material that is stiff against twisting forces but allows for longitudinal compression and/or radial movement.

Furthermore, it will be understood that the sensor assembly and/or prosthesis 700 may advantageously used with a variety of motion-controlled prosthetic and/or orthotic devices, examples of which are described in more detail herein and in U.S. patent application Ser. No. 11/056,344, filed on Feb. 11, 2005, and entitled "SYSTEM AND METHOD FOR MOTION-CONTROLLED FOOT UNIT," which is hereby incorporated by reference herein in its entirety and is to be considered a part of this specification.

While certain embodiments of the inventions have been described, these embodiments have been presented by way of example only, and are not intended to limit the scope of the inventions. Indeed, the novel methods and systems described herein may be embodied in a variety of other forms. For example, the foregoing may be applied to the motion-control of joints other than the ankle, such as a knee or a shoulder. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A system for sensing a rotational movement of a lower-limb prosthetic device, the system comprising:
   a prosthetic foot;
   an attachment member having an upper end and a lower end;
   a pivot assembly rotatably coupling the lower end of the attachment member to the prosthetic foot to allow for rotation of the prosthetic foot about a pivot axis extending through the pivot assembly, wherein the pivot assembly is configured to substantially mimic a natural ankle joint;
   an actuator operatively coupled to the prosthetic foot and to the attachment member, wherein the actuator is configured to actively adjust an angle between the prosthetic foot and the attachment member about the pivot assembly; and
   a sensor assembly coupled to the pivot assembly and configured to detect the rotation of the prosthetic foot about the pivot axis, wherein at least a portion of the sensor assembly is configured to rotate about the pivot axis and is securely positioned along the pivot axis to substantially eliminate other movement, wherein the sensor assembly further comprises a displacement measurement sensor configured to output a signal indicative of the rotation of the rotatable portion of the sensor assembly, wherein the rotatable portion of the sensor assembly comprises a bellow portion having an elongated body that substantially extends along the pivot axis.

2. The system of claim 1, wherein the displacement measurement sensor comprises a potentiometer.

3. The system of claim 1, wherein the bellow portion is configured to at least partially fit within a hollow pivot pin substantially extending along the pivot axis.

4. The system of claim 3, wherein the bellow portion comprises a plurality of ridges configured to limit movement of the bellow portion to rotation about the pivot axis.

5. The system of claim 1, further comprising a control module in communication with the sensor assembly, the control module configured to receive rotation information from the sensor assembly regarding the detected rotation of the prosthetic foot about the pivot axis.

6. The system of claim 5, wherein the control module is configured to determine a gait cycle of a user of the lower-limb prosthetic device based at least on the rotation information.

7. The system of claim 5, wherein the control module is further configured to output, based at least on the rotation information, one or more control signals to control operation of the actuator.

8. The system of claim 7, wherein the one or more control signals is configured to lock the actuator during a selected portion of a gait cycle of a user of the lower-limb prosthetic device.

9. The system of claim 1, wherein the actuator comprises a linear actuator.

10. A system for sensing a rotational movement of a device associated with a limb, the system comprising:
    a foot unit;
    an attachment member having an upper end and a lower end;
    a pivot assembly rotatably coupling the lower end of the attachment member to the foot unit to allow for rotation of the foot unit about an axis extending through the pivot assembly, wherein the pivot assembly is configured to substantially mimic a natural ankle joint;
    an actuator operatively coupled to the foot unit and to the attachment member, wherein the actuator is configured to actively adjust an angle between the foot unit and the attachment member; and
    a sensor assembly coupled to the pivot assembly and configured to detect the rotation of the foot unit about the axis and to substantially neglect axial and radial movement of the foot unit with respect to the axis, wherein the sensor assembly further comprises,
    a potentiometer, and
    an elongated bellow portion coupled to the potentiometer, wherein the elongated bellow portion substantially extends along the axis.

11. The system of claim 10, wherein the elongated bellow portion substantially restricts movement to rotation about the axis.

12. The system of claim 10, wherein the pivot assembly comprises a cylindrical pivot pin extending along the axis and configured to house at least a portion of the elongated bellow portion.

13. The system of claim 10, wherein the foot unit comprises at least one of a prosthesis and an orthosis.

14. The system of claim 10, wherein the sensor assembly further comprises a compression membrane coupling the displacement sensor to a pivot pin of the pivot assembly.

15. A system for sensing a rotational movement of a device associated with a lower limb, the system comprising:
    a foot means for contacting a ground surface;
    a means for attaching the foot means to a patient;
    a means for pivotably coupling the foot means to a lower end of the means for attaching to allow for rotation of the foot means about an axis extending through the means for pivotably coupling, wherein the means for pivotably coupling substantially mimics an ankle joint;
    means for actively adjusting, about the means for pivotably coupling, an angle between the foot means and the means for attaching; and
    a means for sensing coupled to the means for pivotably coupling, the means for sensing further configured to detect the rotation of the foot means about the axis and to substantially neglect axial and radial movement of the foot means with respect to the axis, wherein the means for sensing further comprises,
    a potentiometer, and
    an elongated bellow portion coupled to the potentiometer, wherein the elongated bellow portion is configured to restrict movement of the foot means to rotation about the axis.

* * * * *